(12) United States Patent
Soll et al.

(10) Patent No.: US 9,877,950 B2
(45) Date of Patent: Jan. 30, 2018

(54) PARASITICIDAL COMPOSITIONS COMPRISING AN ISOXAZOLINE ACTIVE AGENT, METHODS AND USES THEREOF

(71) Applicant: MERIAL, INC., Duluth, GA (US)

(72) Inventors: Mark D. Soll, Alpharetta, GA (US); Joseph K. Rosentel, Johns Creek, GA (US); Monica Tejwani-Motwani, Somerset, NJ (US); Carol Belansky, Roselle Park, NJ (US)

(73) Assignee: MERIAL INC., Duluth, GA (US)

( * ) Notice: Subject to any disclaimer, the term of this patent is extended or adjusted under 35 U.S.C. 154(b) by 0 days.

(21) Appl. No.: 14/930,690

(22) Filed: Nov. 3, 2015

(65) Prior Publication Data

US 2016/0051519 A1  Feb. 25, 2016

Related U.S. Application Data

(62) Division of application No. 13/611,025, filed on Sep. 12, 2012, now Pat. No. 9,180,121.

(60) Provisional application No. 61/533,308, filed on Sep. 12, 2011.

(51) Int. Cl.

| | | |
|---|---|---|
| A61K 31/42 | (2006.01) |
| A61K 31/4402 | (2006.01) |
| A61K 31/215 | (2006.01) |
| A61K 31/415 | (2006.01) |
| A61K 31/22 | (2006.01) |
| A61K 31/44 | (2006.01) |
| A61K 45/06 | (2006.01) |
| A61K 38/15 | (2006.01) |
| A61K 31/366 | (2006.01) |
| A61K 31/7048 | (2006.01) |
| A61K 9/00 | (2006.01) |
| A61K 47/10 | (2017.01) |
| A61K 47/14 | (2017.01) |
| A61K 47/26 | (2006.01) |
| A61K 9/06 | (2006.01) |
| A01N 43/40 | (2006.01) |
| A01N 43/80 | (2006.01) |
| A01N 49/00 | (2006.01) |
| A61K 31/231 | (2006.01) |
| A61K 31/4745 | (2006.01) |
| A61K 47/08 | (2006.01) |
| A61K 47/22 | (2006.01) |

(52) U.S. Cl.
CPC ............ *A61K 31/42* (2013.01); *A01N 43/40* (2013.01); *A01N 43/80* (2013.01); *A01N 49/00* (2013.01); *A61K 9/0017* (2013.01); *A61K 9/06* (2013.01); *A61K 31/215* (2013.01); *A61K 31/22* (2013.01); *A61K 31/231* (2013.01); *A61K 31/366* (2013.01); *A61K 31/415* (2013.01); *A61K 31/44* (2013.01); *A61K 31/4402* (2013.01); *A61K 31/4745* (2013.01); *A61K 31/7048* (2013.01); *A61K 38/15* (2013.01); *A61K 45/06* (2013.01); *A61K 47/08* (2013.01); *A61K 47/10* (2013.01); *A61K 47/14* (2013.01); *A61K 47/22* (2013.01); *A61K 47/26* (2013.01)

(58) Field of Classification Search
CPC .... A61K 31/42; A61K 31/22; A61K 31/4402; A61K 31/44; A61K 31/215; A61K 31/415; A61K 38/15; A61K 45/06
USPC .......................... 514/4.6, 345, 357, 380, 407
See application file for complete search history.

(56) References Cited

U.S. PATENT DOCUMENTS

| | | | |
|---|---|---|---|
| 5,904,931 A * | 5/1999 | Lipp | .................... A61K 9/7053 424/447 |
| 6,991,801 B2 | 1/2006 | Soll et al. | |
| 7,662,972 B2 | 2/2010 | Mita et al. | |
| 7,947,715 B2 | 5/2011 | Mita et al. | |
| 7,951,828 B1 | 5/2011 | Mita et al. | |
| 2004/0198676 A1 | 10/2004 | Soll et al. | |
| 2006/0293260 A1 | 12/2006 | Albright | |
| 2009/0076109 A1 | 3/2009 | Miki et al. | |
| 2010/0144797 A1 | 6/2010 | Mita et al. | |
| 2010/0144808 A1 | 6/2010 | Mita et al. | |
| 2010/0179194 A1 | 7/2010 | Mihara et al. | |
| 2010/0179195 A1 | 7/2010 | Lahm et al. | |
| 2010/0254960 A1 | 10/2010 | Long et al. | |
| 2011/0009438 A1 | 1/2011 | Mita et al. | |
| 2011/0059988 A1 | 3/2011 | Heckeroth et al. | |
| 2011/0118212 A1 | 5/2011 | Koerber et al. | |

(Continued)

FOREIGN PATENT DOCUMENTS

| | | |
|---|---|---|
| JP | 11-49669 | 2/1999 |
| JP | 11-335277 | 12/1999 |
| JP | 2004-269368 | 9/2004 |
| WO | 2007/054818 | 5/2007 |
| WO | 2007/070606 | 6/2007 |
| WO | 2007/075459 | 7/2007 |
| WO | 2007/079162 | 7/2007 |

(Continued)

OTHER PUBLICATIONS

"Cosolvency of Dimethyl Isosorbide for Steroid Solubility", Zia Hossein et al., Pharmaceutical Research, Apr. 1, 1991, vol. 8, No. 4, pp. 502-504.

*Primary Examiner* — Yih-Horng Shiao
(74) *Attorney, Agent, or Firm* — Judy Jarecki-Black; John Ezcurra; Merial Inc.

(57) ABSTRACT

This invention relates to topical compositions for combating ectoparasites and endoparasites in animals, comprising at least one isoxazoline active agent and a pharmaceutically acceptable carrier, optionally in combination with one or more additional active agents. This invention also provides for an improved methods for eradicating, controlling, and preventing parasite infections and infestations in an animal comprising administering the compositions of the invention to the animal in need thereof.

36 Claims, 3 Drawing Sheets

(56) References Cited

U.S. PATENT DOCUMENTS

| | | |
|---|---|---|
| 2011/0015231 A1 | 6/2011 | Le Hir de Fallois et al. |
| 2011/0159107 A1 | 6/2011 | Koerber et al. |
| 2011/0166193 A1 | 7/2011 | Renold et al. |
| 2011/0245191 A1 | 10/2011 | Rosentel, Jr. et al. |
| 2011/0257011 A1 | 10/2011 | Kaiser et al. |
| 2012/0030841 A1 | 2/2012 | Koerber et al. |
| 2012/0035122 A1 | 2/2012 | Vaillancourt et al. |
| 2012/0077765 A1 | 3/2012 | Curtis et al. |

FOREIGN PATENT DOCUMENTS

| | | |
|---|---|---|
| WO | 2007/123855 | 11/2007 |
| WO | 2008/030385 | 3/2008 |
| WO | 2009/002809 | 12/2008 |
| WO | 2009/018198 | 2/2009 |
| WO | 2010/003923 | 1/2010 |
| WO | 2010/079077 | 7/2010 |
| WO | 2010/084067 | 7/2010 |
| WO | 2011/067272 | 6/2011 |
| WO | 2011/092287 | 8/2011 |
| WO | 2011/104087 | 9/2011 |
| WO | 2011/149749 | 12/2011 |
| WO | 2011/154433 | 12/2011 |
| WO | 2011/154434 | 12/2011 |
| WO | 2011/154494 | 12/2011 |
| WO | 2011/157733 | 12/2011 |
| WO | 2012/007426 | 1/2012 |
| WO | 2012/038851 | 3/2012 |
| WO | 2012/089622 | 7/2012 |
| WO | 2012/089623 | 7/2012 |

* cited by examiner

PARASITICIDAL COMPOSITIONS COMPRISING AN ISOXAZOLINE ACTIVE AGENT, METHODS AND USES THEREOF

CROSS REFERENCE TO RELATED APPLICATIONS

This application is a divisional application of U.S. patent application Ser. No. 13/611,025 filed Sep. 12, 2012, which claims the benefit of priority to U.S. Provisional Application No. 61/533,308 filed Sep. 12, 2011, each of which are incorporated herein by reference in their entirety.

FIELD OF THE INVENTION

The present invention provides topical veterinary compositions comprising at least one isoxazoline active agent for controlling ectoparasites and endoparasites in animals; the use of these compositions against ectoparasites and/or endoparasites, and methods for preventing or treating parasitic infections and infestations in animals.

BACKGROUND OF THE INVENTION

Animals such as mammals and birds are often susceptible to parasite infestations/infections. These parasites may be ectoparasites, such as insects, and endoparasites such as filariae and other worms. Domesticated animals, such as cats and dogs, are often infested with one or more of the following ectoparasites:
- fleas (e.g. *Ctenocephalides* spp., such as *Ctenocephalides felis* and the like);
- ticks (e.g. *Rhipicephalus* spp., *Ixodes* spp., *Dermacentor* spp., *Amblyoma* spp., and the like);
- mites (e.g. *Demodex* spp., *Sarcoptes* spp., *Otodectes* spp., and the like);
- lice (e.g. *Trichodectes* spp., *Cheyletiella* spp., *Lignonathus* spp. and the like);
- mosquitoes (*Aedes* spp., *Culux* spp., *Anopheles* spp. and the like); and
- flies (*Hematobia* spp., *Musca* spp., *Stomoxys* spp., *Dematobia* spp., *Coclyomia* spp. and the like).

Fleas are a particular problem because not only do they adversely affect the health of the animal or human, but they also cause a great deal of psychological stress. Moreover, fleas are also vectors of pathogenic agents in animals and humans, such as dog tapeworm (*Dipylidium caninum*).

Similarly, ticks are also harmful to the physical and psychological health of the animal or human. However, the most serious problem associated with ticks is that they are the vector of pathogenic agents in both humans and animals. Major diseases which are caused by ticks include borrelioses (Lyme disease caused by *Borrelia burgdorferi*), babesioses (or piroplasmoses caused by *Babesia* spp.) and rickettsioses (also known as Rocky Mountain spotted fever). Ticks also release toxins which cause inflammation or paralysis in the host. Occasionally, these toxins are fatal to the host.

Likewise, farm animals are also susceptible to parasite infestations. For example, cattle are affected by a large number of parasites. A parasite which is very prevalent among farm animals is the tick genus *Rhipicephalus*, especially those of the species *microplus* (cattle tick), *decoloratus* and *annulatus*. Ticks such as *Rhipicephalus microplus* (formerly *Boophilus microplus*) are particularly difficult to control because they live in the pasture where farm animals graze. This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest found on buffalo, horses, donkeys, goats, sheep, deer, pigs, and dogs. A heavy tick burden on animals can decrease production and damage hides as well as transmit diseases such as babesiosis ("cattle fever") and anaplasmosis caused by protozoan parasites.

Animals and humans also suffer from endoparasitic infections including, for example, helminthiasis which is most frequently caused by a group of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting domestic animals and poultry. Other parasites which occur in the gastrointestinal tract of animals and humans include *Ancylostoma, Necator, Ascaris, Strongyloides, Trichinella, Capillaria, Toxocara, Toxascaris, Trichiris, Enterobius* and parasites which are found in the blood or other tissues and organs such as filarial worms and the extra intestinal stages of *Strogyloides, Toxocara* and *Trichinella*.

Recently, isoxazole and isoxazoline-containing compounds have been demonstrated to be effective against parasites that harm animals. For example, US 2010/0234219 A1 (to DuPont) discloses isoxazoline compounds according to Formula (I) below, which are active against ectoparasites and/or endoparasites.

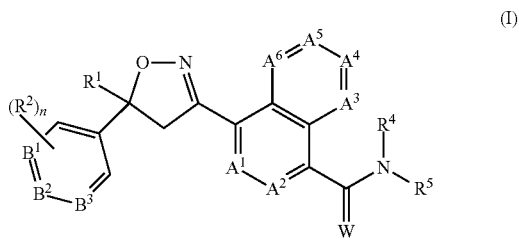

(I)

In addition, published patent application nos. US 2010/0254960 A1, WO 2007/070606 A2, WO 2007/123855 A2, WO 2010/003923 A1, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1 and WO 2007/075459 A2 and U.S. Pat. Nos. 7,951,828 and 7,662,972 describe various other parasiticidal isoxazoline compounds. WO 2012/089623 describes topical localized isoxazoline formulations comprising glycofurol.

Notwithstanding the compositions comprising isoxazoline active agents alone or in combination with other active agents described in the documents above, there is a need for veterinary compositions and methods with improved efficacy, bioavailability, and spectrum of coverage to protect animals against endoparasites and/or ectoparasites. Optimal compositions should provide contact and/or systemic activity, be efficacious, have a quick onset of activity, have a long duration of activity, and be safe to the animal recipient and their human owners. This invention addresses this need.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention is directed to topical compositions comprising at least one isoxazoline, alone or in combination with other active agents, and their use to control parasites in or on warm-blooded animals and birds. In accordance with this invention, it has been discovered that these compositions generally show desirable bioavailability, and can provide contact and/or systemic activity. The compositions also provide desirable safety profiles toward the warm-blooded and bird animal recipients. In addition, it has been discovered that a single administration of such compositions generally provides potent activity against one or more ectoparasites, while also tending to provide fast onset of activity, long duration of activity, and/or desirable safety profiles.

The invention encompasses uses or veterinary uses of the isoxazoline compositions for the treatment or prophylaxis of parasitic infections and infestations of animals (either wild or domesticated), including livestock and companion animals such as cats, dogs, horses, chickens, sheep, goats, pigs, turkeys and cattle, with the aim of ridding these hosts of parasites commonly encountered by such animals.

In a particularly preferred embodiment, the composition is a topical spot-on formulation. In another preferred embodiment particularly well suited for livestock animals, the composition is a topical pour-on formulation. The invention also includes other topical compositions comprising an isoxazoline active agent including sprays, aerosols, foams and the like.

In some embodiments, the topical veterinary composition comprises a pharmaceutically acceptable carrier wherein the carrier comprises a diester of a dicarboxylic acid, a glycol ester, a glycol ether, a fatty acid ester, a polyethylene glycol, or polyethylene glycol ester, an oil, an alcohol, a glycerol ester, a glycerol ether, propylene glycol, ethylene glycol, a glycol carbonate, dimethyl isosorbide, N-methylpyrrolidone, or a mixture thereof.

In one embodiment, the diester of a dicarboxylic acid is a diester of a $C_6$-$C_{16}$ dicarboxylic acid including, but not limited to, diethyl sebacate or diisopropyl adipate.

In another embodiment of the invention, the pharmaceutically acceptable carrier of the compositions comprises mixture of a diester of a dicarboxylic acid and a propylene glycol ester, a fatty acid ester, a polyethylene glycol ester, a polyethylene glycol, an oil, a $C_6$-$C_{20}$ long-chain aliphatic alcohol, a $C_1$-$C_8$ alcohol, glycol ether, or a combination thereof.

In certain embodiments, the pharmaceutically acceptable carrier of the topical veterinary composition of the invention further comprises a mixed ester of sucrose and acetic and isobutyric acid, a low melting wax, a hard fat or a block co-polymer of ethylene oxide and propylene oxide, or a combination thereof.

In another embodiment, the pharmaceutically acceptable carrier comprises dimethyl isosorbide, glycerol formal, propylene carbonate, triacetin, diethyleneglycol monoethyl ether, polyethylene glycol 400 or benzyl alcohol, or a mixture thereof.

The invention also provides methods for the treatment or prevention of parasitic infections and infestations in animals, comprising administering an effective amount of a composition comprising at least one isoxazoline to the animal. Surprisingly, it has been found that the inventive compositions and formulations described herein exhibit superior broad spectrum efficacy against harmful ectoparasites more rapidly, and over a long duration compared to compositions known in the art.

In one embodiment, the invention provides topical veterinary compositions comprising effective amounts of at least one isoxazoline of formula (I) below, in combination and a pharmaceutically or veterinarily acceptable liquid carrier, where variables $A^1$, $A^2$, $A^3$, $A^4$, $A^5$, $A^6$, $B^1$, $B^2$, $B^3$, $R^1$, $R^2$, $R^3$, $R^4$, $R^5$, W are defined herein.

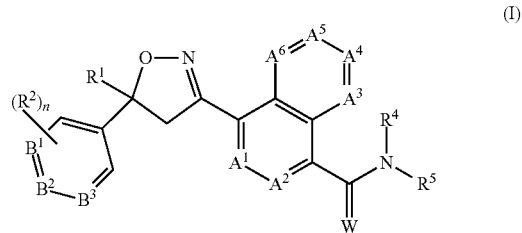

(I)

In some embodiments, the topical veterinary compositions and methods comprise 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide as the active agent.

In other embodiments, the compositions may further comprise one or more additional active agents. In one embodiment, the compositions comprise at least one macrocyclic lactone active agent, including, but not limited to, avermectins or milbemycins. In some embodiments, the avermectin or milbemycin active agent is eprinomectin, ivermectin, selamectin, milbemectin, milbemycin D, milbemycin oxime, or moxidectin.

In another embodiment, the topical compositions of the invention include a combination of an isoxazoline active agent with the neonicotinoid active agent nitenpyram.

In other embodiments, the compositions and methods of the invention may further comprise an insect growth regulator (IGR) active agent, including but not limited to, methoprene, pyriproxyfen, hydroprene, cyromazine, fluazuron, lufenuron, or novaluron. In another preferred embodiment, the compositions of the invention comprise a neonicotinoid active agent such as nitenpyram. In other embodiments, the compositions and methods comprise at least one of thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, or an aryloazol-2-yl cyanoethylamino active agent.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

DETAILED DESCRIPTION

Figure 1:
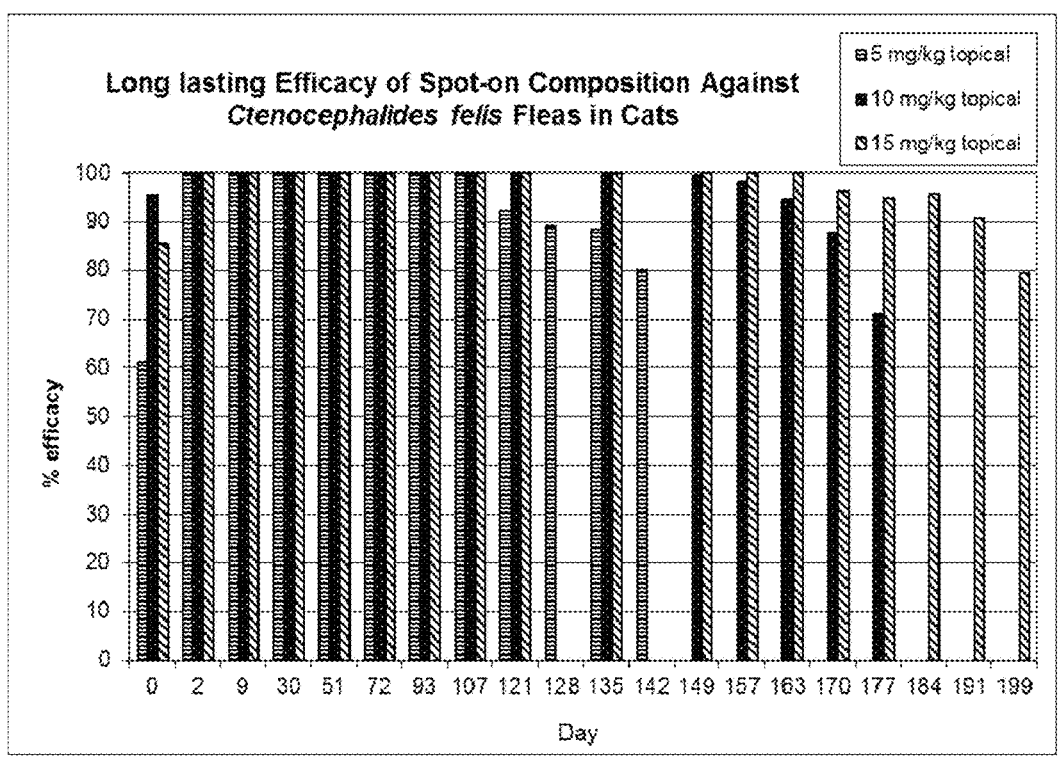
FIG. 1 is a plot showing the long lasting efficacy of a spot-on composition comprising Compound A against *Ctenocephalides felis* fleas in cats (Example 9).

The present invention provides novel and inventive topical compositions comprising at least one isoxazoline compound together with a pharmaceutically acceptable carrier or diluent that is suitable for topical application to an animal.

In some embodiments of the invention, the compositions preferably include spot-on or pour-on formulations that are applied to a localized area on an animal. Topical spray, aerosol or foam formulations, which typically include the active agent in lower concentrations, are also encompassed by the invention. These formulations provide surprisingly effective protection of the animals against parasites for an extended period of time. The formulations also provide extremely rapid killing of parasites infesting animals.

Also provided are methods and uses for the treatment and/or prophylaxis of parasitic infections and infestations of animals, comprising administering an effective amount of a formulation of the invention to the animal.

The invention includes at least the following features:

(a) topical veterinary formulations that exhibit superior activity against animal parasites comprising at least one isoxazoline active agent together with a pharmaceutically acceptable carrier or diluent that is suitable for topical application to an animal;

(b) topical veterinary compositions that exhibit superior long lasting efficacy that comprise at least one isoxazoline compound of formula (I) described herein together with a pharmaceutically acceptable carrier or diluent that is suitable for topical application to an animal;

(c) topical veterinary compositions that exhibit superior long lasting efficacy that comprise at least one isoxazoline active agent in combination with one or more other active agents together with a pharmaceutically acceptable carrier or diluent that is suitable for topical application to an animal;

(d) topical veterinary compositions comprising an effective amount of an isoxazoline active agent together with a pharmaceutically acceptable carrier or diluent that is suitable for topical application to an animal, wherein the carrier does not comprise glycofurol;

(e) topical veterinary compositions comprising an effective amount of an isoxazoline active agent together with a pharmaceutically acceptable carrier or diluent that is suitable for topical application to an animal, wherein the carrier is not a binary mixture of propylene glycol and glycerol formal;

(f) methods for the treatment or prevention of parasitic infections and infestations in an animal comprising administering an effective amount of a composition comprising at least one isoxazoline active agent together with a pharmaceutically acceptable carrier or diluent;

(g) methods for the treatment or prevention of parasitic infections and infestations in an animal comprising administering an effective amount of a composition comprising at least one isoxazoline active agent with a pharmaceutically acceptable carrier or diluent that is suitable for topical application to an animal;

(h) methods for the treatment or prevention of parasitic infections and infestations in an animal comprising administering an effective amount of a topical composition comprising at least one isoxazoline active agent in combination with one or more other active agents together with a pharmaceutically acceptable carrier or diluent that is suitable for topical application to an animal;

(i) use of veterinary compositions comprising at least one isoxazoline compound, including a compound of formula (I), together with a pharmaceutically acceptable carrier or diluent in the prevention or treatment of animal parasites.

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

DEFINITIONS

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

The term "fatty acid" refers to carboxylic acids having from 4 to 26 carbon atoms.

The terms "fatty alcohol" or "long-chain aliphatic alcohol" refer to aliphatic alcohols containing from 6 to 20 carbon atoms.

The term "low melting" refers to substances that are solids at room temperature but melt into liquids below 50° C.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, (CH$_3$)$_2$CH—CH$_2$O—, (CH$_3$)$_3$CO—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include C$_6$-C$_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The terms "aralkyl" or "arylalkyl" refers to an aryl group that is bonded to the parent compound through a diradical alkylene bridge, (—CH$_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$)).

Stereoisomers and Polymorphic Forms

It will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents. In some embodiments, the compositions of the invention may include up to 15% (w/w), up to 20% (w/w), or up to 30% (w/w) of a particular solid form.

Salts

Also contemplated within the scope of the invention are acid or base salts, where applicable, of the compounds of the invention provided for herein.

The term "acid salt" contemplates salts of the compounds with all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base salt" contemplates salts of the compounds with all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

In one embodiment, the invention provides topical veterinary compositions comprising effective amounts of at least one isoxazoline of formula (I) below, in combination and a pharmaceutically or veterinarily acceptable liquid carrier:

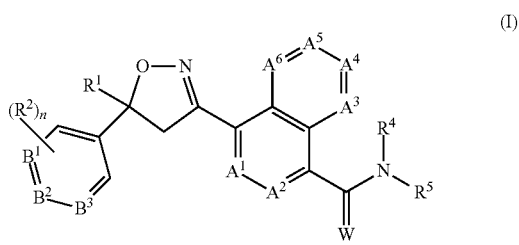

(I)

wherein $A^1$, $A^2$, $A^3$, $A^4$, $A^5$ and $A^6$ are independently $CR^3$ or N, provided that at most 3 of $A^1$, $A^2$, $A^3$, $A^4$, $A^5$ and $A^6$ are N;

$B^1$, $B^2$ and $B^3$ are independently $CR^2$ or N;

W is O or S;

$R^1$ is alkyl, alkenyl, alkynyl, cycloalkyl, alkylcycloalkyl or cycloalkylalkyl, each optionally substituted with one or more substituents independently selected from $R^6$;

each $R^2$ is independently H, halogen, alkyl, haloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —$NO_2$;

each $R^3$ is independently H, halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN or —$NO_2$;

$R^4$ is H, alkyl, alkenyl, alkynyl, cycloalkyl, alkylcycloalkyl, cycloalkylalkyl, alkylcarbonyl or alkoxycarbonyl;

$R^5$ is H, $OR^{10}$, $NR^{11}R^{12}$ or $Q^1$; or alkyl, alkenyl, alkynyl, cycloalkyl, alkylcycloalkyl or cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —$NO_2$ and alkoxy;

each $R^6$ is independently halogen, alkyl, alkoxy, alkylthio, alkylsulfinyl, alkylsulfonyl, —CN or —$NO_2$;

each $R^7$ is independently halogen; alkyl, cycloalkyl, alkoxy, alkylthio, alkylsulfinyl, alkylsulfonyl, alkylamino, dialkylamino, cycloalkylamino, alkylcarbonyl, alkoxycarbonyl, alkylaminocarbonyl, dialkylaminocarbonyl, haloalkylcarbonyl, haloalkoxycarbonyl, haloalkylaminocarbonyl, dihaloalkylaminocarbonyl, hydroxy, —$NH_2$, —CN or —$NO_2$; or $Q^2$;

each $R^8$ is independently halogen, alkoxy, haloalkoxy, alkylthio, haloalkylthio, alkylsulfinyl, haloalkylsulfinyl, alkylsulfonyl, haloalkylsulfonyl, alkylamino, dialkylamino, alkoxycarbonyl, —CN or —$NO_2$;

each $R^9$ is independently halogen, alkyl, haloalkyl, cycloalkyl, halocycloalkyl, alkoxy, haloalkoxy, alkylthio, haloalkylthio, alkylsulfinyl, haloalkylsulfinyl, alkylsulfonyl, haloalkylsulfonyl, alkylamino, dialkylamino, —CN, —NO$_2$, phenyl or pyridinyl;

$R^{10}$ is H; or alkyl, alkenyl, alkynyl, cycloalkyl, alkylcycloalkyl or cycloalkylalkyl, each optionally substituted with one of more halogen;

$R^{11}$ is H, alkyl, alkenyl, alkynyl, cycloalkyl, alkylcycloalkyl, cycloalkylalkyl, alkylcarbonyl or alkoxycarbonyl;

$R^{12}$ is H; $Q^3$; or alkyl, alkenyl, alkynyl, cycloalkyl, alkylcycloalkyl or cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of alkyl, halogen, —CN, —NO$_2$ and alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2.

In one embodiment, the invention provides topical veterinary compositions comprising effective amounts of at least one isoxazoline of formula (I) below, in combination and a pharmaceutically or veterinarily acceptable liquid carrier:

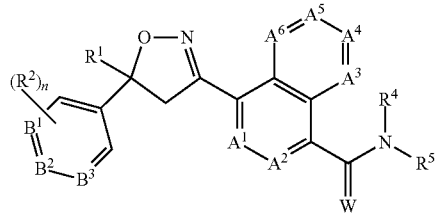

(I)

wherein:

$A^1$, $A^2$, $A^3$, $A^4$, $A^5$ and $A^6$ are independently $CR^3$ or N, provided that at most 3 of $A^1$, $A^2$, $A^3$, $A^4$, $A^5$ and $A^6$ are N;

$B^1$, $B^2$ and $B^3$ are independently $CR^2$ or N;

W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO$_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, —NH$_2$, —CN or —NO$_2$; or $Q_2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^{11}$ and $R^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;

$Q^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from $R^8$;

each $Q^2$ is independently a phenyl ring or a 5- or 6-membered heterocyclic ring, each ring optionally substituted with one or more substituents independently selected from $R^9$;

$Q^3$ is a phenyl ring or a 5- or 6-membered heterocyclic ring, each ring optionally substituted with one or more substituents independently selected from $R^9$; and n is 0, 1 or 2.

In one embodiment of formula (I), W is O. In another embodiment, W is S.

In another embodiment of formula (I), $A^1$, $A^2$, $A^3$, $A^4$, $A^5$ and $A^6$ are each $CR^3$.

In another embodiment of formula (I), $B^1$, $B^2$ and $B^3$ are each $CR^2$.

In still another embodiment of formula (I), W is O and $A^1$, $A^2$, $A^3$, $A^4$, $A^5$ and $A^6$ are each $CR^3$.

In yet another embodiment of formula (I), W is O; $A^1$, $A^2$, $A^3$, $A^4$, $A^5$ and $A^6$ are each $CR^3$; and $B^1$, $B^2$ and $B^3$ are each $CR^2$.

In another embodiment of formula (I), $A^1$, $A^2$, $A^3$, $A^4$, $A^5$ and $A^6$ are each CH.

In another embodiment of formula (I), $B^1$, $B^2$ and $B^3$ are each $CR^2$; and $R^2$ is H, halogen, $C_1$-$C_6$ alkyl or $C_1$-$C_6$ haloalkyl.

In still another embodiment of formula (I), $R^1$ is $C_1$-$C_3$ alkyl optionally substituted by one or more of $R^6$;

$R^2$ is independently H, halogen, $C_1$-$C_6$ haloalkyl, $C_1$-$C_6$ haloalkoxy or —CN; and each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, —CN or —NO$_2$.

In still another embodiment, the invention provides a composition comprising an isoxazoline of formula (I) wherein:

W is O or S; $R^4$ is H or $C_1$-$C_6$ alkyl; $R^5$ is —CH$_2$C(O) NHCH$_2$CF$_3$; each of $A^1$=$A^2$=$A^3$=$A^4$=$A^5$=$A^6$ is CH;
$R^1$ is $C_1$-$C_6$ alkyl each optionally substituted with one or more substituents independently selected from $R^6$;
$R^6$ is halogen or $C_1$-$C_6$ alkyl; and
$B^1$, $B^2$, and $B^3$ are independently CH, C-halogen, C—$C_1$-$C_6$ alkyl, C—$C_1$-$C_6$ haloalkyl, or C—$C_1$-$C_6$ alkoxy.

In another embodiment of formula (I), $B^1$, $B^2$ and $B^3$ are independently $CR^2$;

W is O;

$R^4$ is H, $C_1$-$C_6$ alkyl, $C_2$-$C_7$ alkylcarbonyl or $C_2$-$C_7$ alkoxycarbonyl; and $R^5$ is H, NR$^{11}$R$^{12}$ or $Q^1$; or $C_1$-$C_4$ alkyl, $C_2$-$C_4$ alkenyl, $C_2$-$C_4$ alkynyl, $C_3$-$C_4$ cycloalkyl, $C_4$-$C_7$ alkylcycloalkyl or $C_4$-$C_7$ cycloalkylalkyl, each optionally substituted with one or more of $R^7$.

In still another embodiment of formula (I), $R^1$ is $C_1$-$C_3$ alkyl optionally substituted with halogen;

each $R^2$ is independently H, CF$_3$, OCF$_3$, halogen or —CN;

each $R^3$ is independently H, $C_1$-$C_4$ alkyl, $C_1$-$C_4$ haloalkyl, $C_3$-$C_6$ cycloalkyl, $C_1$-$C_4$ alkoxy or —CN; and each $R^7$ is independently halogen, $C_1$-$C_4$ alkyl, $C_1$-$C_4$ alkoxy, $C_1$-$C_4$ alkylthio, $C_1$-$C_4$ alkylsulfinyl, $C_1$-$C_4$ alkylsulfonyl, $C_2$-$C_4$ alkylcarbonyl, $C_2$-$C_4$ alkoxycarbonyl, $C_2$-$C_5$ alkylaminocarbonyl, $C_2$-$C_5$ haloalkylcarbonyl, $C_2$-$C_5$ haloalkoxycarbonyl, $C_2$-$C_5$ haloalkylaminocarbonyl, —NH$_2$, —CN or NO$_2$; or $Q^2$.

In yet another embodiment of formula (I), $R^4$ is H;

$R^5$ is $C_1$-$C_4$ alkyl optionally substituted with one or more $R^7$;

each $R^7$ is independently halogen or $Q^2$; and each $Q^2$ is independently phenyl, pyridinyl or thiazolyl.

In still another embodiment of formula (I), $R^1$ is CF$_3$;

$A^1$, $A^2$, $A^3$, $A^4$, $A^5$ and $A^6$ are each $CR^3$;

$B^2$ is $CR^2$; and each $R^3$ is independently H, $C_1$-$C_4$ alkyl or —CN.

In another embodiment, $B^2$ is CH;

$B^1$ and $B^3$ are each $CR^2$ where each $R^2$ is independently halogen or $C_1$-$C_3$ haloalkyl;

$A^1$, $A^2$, $A^3$, $A^4$, $A^5$ and $A^6$ are each $CR^3$;

$R^3$ is H; and n is 2.

In still another embodiment of formula (I), $R^1$ is CF$_3$;

$A^1$, $A^2$, $A^3$, $A^4$, $A^5$ and $A^6$ are each $CR^3$;

$B^2$ is CH;

each of $B^1$ and $B^3$ are $CR^2$;

each $R^3$ is independently H or $C_1$-$C_4$ alkyl;

each $R^2$ is independently halogen or $C_1$-$C_3$ haloalkyl;

$R^4$ is H;

$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl.

In yet another embodiment of formula (I), $R^1$ is CF$_3$;

$A^1$, $A^2$, $A^3$, $A^4$, $A^5$ and $A^6$ are each CH;

$B^2$ is CH;

each of $B^1$ and $B^3$ are $CR^2$;

each $R^2$ is independently halogen or $C_1$-$C_3$ haloalkyl;

$R^4$ is H;

$R^5$ is $C_1$-$C_4$ alkyl optionally substituted with one or more $R^7$; and $R^7$ is $C_2$-$C_7$ alkylaminocarbonyl, $C_3$-$C_9$ dialkylaminocarbonyl, $C_2$-$C_7$ haloalkylaminocarbonyl or $C_3$-$C_9$ dihaloalkylaminocarbonyl.

In a preferred embodiment, a topical composition comprising an isoxazoline active agent of formula (I) is provided, wherein:

$R^1$ is CF$_3$;

W is O;

$A^1$, $A^2$, $A^3$, $A^4$, $A^5$ and $A^6$ are each CH;

$B^2$ is CH;

$B^1$ is chloro;

$B^2$ is CF3;

$R^4$ is H;

$R^5$ is CH$_2$C(O)NHCH$_2$CF$_3$; and n is 2.

In a preferred embodiment, the isoxazoline compound is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound A).

In another embodiment, the compositions of the invention may include one or more compounds of the isoxazolines disclosed in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In other preferred embodiments, the invention provides topical compositions comprising an isoxazoline active agent described in WO 2009/02451A2 and WO 2011/075591A1, both incorporated herein by reference in their entirety, in combination with a pharmaceutically acceptable carrier or diluent.

In another preferred embodiment, the invention provides topical compositions comprising compound 11-1 described in WO 2009/02451A2, which has the structure:

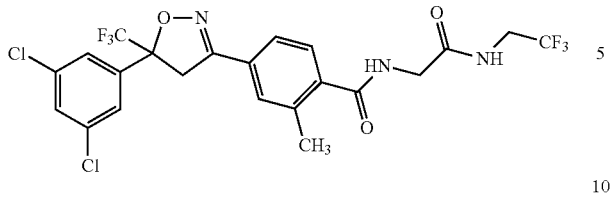

in combination with a pharmaceutically acceptable carrier or diluent described herein.

In still another embodiment the invention provides topical compositions comprising one or more of the isoxazoline compounds of formulae 1.001 to 1.025 and 2.001 to 2.018 described in WO 2011075591 in combination with a pharmaceutically acceptable carrier described herein:

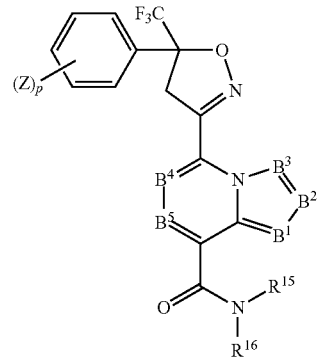

Compounds 1.001 to 1.025

| Compound No. | $(Z)_p$ | $B^5$ | $B^4$ | $B^3$ | $B^2$ | $B^1$ | $R^{15}$ | $R^{16}$ | MS MH+ | RT (min) | LCMS Method |
|---|---|---|---|---|---|---|---|---|---|---|---|
| 1.001 | 3,5-Cl$_2$ | C—H | C—H | C—H | C—H | N | H | CH$_2$C(O)NHCH$_2$CF$_3$ | 582 | 2.21 | 1 |
| 1.002 | 3,5-Cl$_2$ | C—H | C—H | C—H | C—H | N | H | CH$_2$CF$_3$ | 525 | 2.32 | 1 |
| 1.003 | 3,5-(CF$_3$)$_2$ | C—H | C—H | C—H | C—H | N | CH$_3$ | CH$_2$CO$_2$CH$_3$ | 597 | 2.06 | 1 |
| 1.004 | 3,5-(CF$_3$)$_2$ | C—H | C—H | C—H | C—H | N | CH$_3$ | CH$_2$CO$_2$H | 583 | 2.07 | 1 |
| 1.005 | 3,5-(CF$_3$)$_2$ | C—H | C—H | C—H | C—H | N | CH$_3$ | CH$_2$C(O)NHCH$_2$CF$_3$ | 664 | 2.14 | 1 |
| 1.006 | 3,5-(CF$_3$)$_2$ | C—H | C—H | C—H | C—H | N | H | CH$_2$C(O)NHCH$_2$CF$_3$ | 650 | 2.18 | 1 |
| 1.007 | 3,5-(CF$_3$)$_2$ | C—H | C—H | C—H | C—H | N | H | CH$_2$CH$_2$SCH$_3$ | 585 | 2.31 | 1 |
| 1.008 | 3,5-(CF$_3$)$_2$ | C—H | C—H | C—H | C—H | C—H | H | CH$_2$C(O)NHCH$_2$CF$_3$ | 648 | 2.18 | 1 |
| 1.009 | 3,5-(CF$_3$)$_2$ | C—H | C—H | C—H | C—H | C—H | H | CH$_2$CH$_2$SCH$_3$ | 584 | 2.24 | 1 |
| 1.010 | 3,5-(CF$_3$)$_2$ | C—H | C—H | C—H | C—H | C—H | H | CH$_2$CF$_3$ | | | |
| 1.011 | 3,5-Cl$_2$ | C—H | C—H | C—H | C—H | C—H | H | CH$_2$C(O)NHCH$_2$CF$_3$ | 581 | 2.20 | 1 |
| 1.012 | 3,5-Cl$_2$ | C—H | C—H | C—H | C—H | C—H | H | CH$_2$CF$_3$ | | | |
| 1.013 | 3,5-Cl$_2$ | C—H | C—H | C—H | C—H | C—H | H | CH$_2$CH$_2$SCH$_3$ | 516 | 2.26 | 1 |
| 1.014 | 3-Cl, 5-CF$_3$ | C—H | C—H | C—H | C—H | C—H | H | CH$_2$C(O)NHCH$_2$CF$_3$ | | | |
| 1.015 | 3-Cl, 5-CF$_3$ | C—H | C—H | C—H | C—H | C—H | H | CH$_2$CF$_3$ | | | |
| 1.016 | 3-Cl, 5-CF$_3$ | C—H | C—H | C—H | C—H | C—H | H | CH$_2$CH$_2$SCH$_3$ | | | |
| 1.017 | 3,5-Cl$_2$ | C—H | C—H | C—Me | C—H | C—Me | H | CH$_2$C(O)NHCH$_2$CF$_3$ | 609 | 2.12 | 1 |
| 1.018 | 3,5-Cl$_2$ | C—H | C—H | C—Me | C—H | C—Me | H | CH$_2$CF$_3$ | 552 | 2.17 | 1 |
| 1.019 | 3,5-Cl$_2$ | C—H | C—H | C—Me | C—H | C—Me | H | CH$_2$CH$_2$SCH$_3$ | 544 | 2.18 | 1 |
| 1.020 | 3,5-(CF$_3$)$_2$ | C—H | C—H | C—Me | C—H | C—Me | H | CH$_2$C(O)NHCH$_2$CF$_3$ | | | |
| 1.021 | 3,5-(CF$_3$)$_2$ | C—H | C—H | C—Me | C—H | C—Me | H | CH$_2$CF$_3$ | | | |
| 1.022 | 3,5-(CF$_3$)$_2$ | C—H | C—H | C—Me | C—H | C—Me | H | CH$_2$CH$_2$SCH$_3$ | | | |
| 1.023 | 3-Cl, 5-CF$_3$ | C—H | C—H | C—Me | C—H | C—Me | H | CH$_2$C(O)NHCH$_2$CF$_3$ | | | |
| 1.024 | 3-Cl, 5-CF$_3$ | C—H | C—H | C—Me | C—H | C—Me | H | CH$_2$CF$_3$ | | | |
| 1.025 | 3-Cl, 5-CF$_3$ | C—H | C—H | C—Me | C—H | C—Me | H | CH$_2$CH$_2$SCH$_3$ | | | |

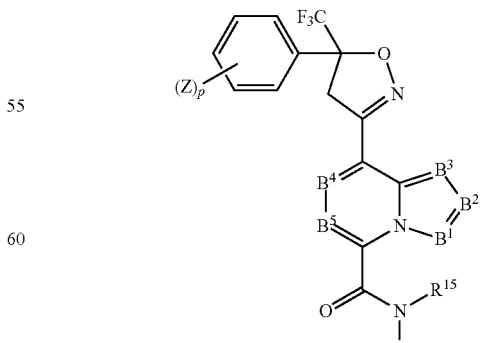

Compounds 2.001 to 2.018

| Compound No. | $(Z)_p$ | $B^5$ | $B^4$ | $B^3$ | $B^2$ | $B^1$ | $R^{15}$ | $R^{16}$ | MS MH+ | RT (min) | LCMS Method |
|---|---|---|---|---|---|---|---|---|---|---|---|
| 2.001 | 3,5-Cl$_2$ | C—H | C—H | N | C—H | C—H | H | CH$_2$C(O)NHCH$_2$CF$_3$ | | | |
| 2.002 | 3,5-Cl$_2$ | C—H | C—H | N | C—H | C—H | H | CH$_2$CF$_3$ | | | |
| 2.003 | 3,5-Cl$_2$ | C—H | C—H | N | C—H | C—H | H | CH$_2$CH$_2$SCH$_3$ | | | |
| 2.004 | 3,5-(CF$_3$)$_2$ | C—H | C—H | N | C—H | C—H | H | CH$_2$C(O)NHCH$_2$CF$_3$ | 650 | 1.85 | 1 |
| 2.005 | 3,5-(CF$_3$)$_2$ | C—H | C—H | N | C—H | C—H | H | CH$_2$CF$_3$ | | | |
| 2.006 | 3,5-(CF$_3$)$_2$ | C—H | C—H | N | C—H | C—H | H | CH$_2$CH$_2$SCH$_3$ | | | |
| 2.007 | 3-Cl, 5-CF$_3$ | C—H | C—H | N | C—H | C—H | H | CH$_2$C(O)NHCH$_2$CF$_3$ | | | |
| 2.008 | 3-Cl, 5-CF$_3$ | C—H | C—H | N | C—H | C—H | H | CH$_2$CF$_3$ | | | |
| 2.009 | 3-Cl, 5-CF$_3$ | C—H | C—H | N | C—H | C—H | H | CH$_2$CH$_2$SCH$_3$ | | | |
| 2.010 | 3,5-Cl$_2$ | C—H | C—H | C—H | C—H | C—H | H | CH$_2$C(O)NHCH$_2$CF$_3$ | | | |
| 2.011 | 3,5-Cl$_2$ | C—H | C—H | C—H | C—H | C—H | H | CH$_2$CF$_3$ | | | |
| 2.012 | 3,5-Cl$_2$ | C—H | C—H | C—H | C—H | C—H | H | CH$_2$CH$_2$SCH$_3$ | | | |
| 2.013 | 3,5-(CF$_3$)$_2$ | C—H | C—H | C—H | C—H | C—H | H | CH$_2$C(O)NHCH$_2$CF$_3$ | | | |
| 2.014 | 3,5-(CF$_3$)$_2$ | C—H | C—H | C—H | C—H | C—H | H | CH$_2$CF$_3$ | | | |
| 2.015 | 3,5-(CF$_3$)$_2$ | C—H | C—H | C—H | C—H | C—H | H | CH$_2$CH$_2$SCH$_3$ | | | |
| 2.016 | 3-Cl, 5-CF$_3$ | C—H | C—H | C—H | C—H | C—H | H | CH$_2$C(O)NHCH$_2$CF$_3$ | | | |
| 2.017 | 3-Cl, 5-CF$_3$ | C—H | C—H | C—H | C—H | C—H | H | CH$_2$CF$_3$ | | | |
| 2.018 | 3-Cl, 5-CF$_3$ | C—H | C—H | C—H | C—H | C—H | H | CH$_2$CH$_2$SCH$_3$ | | | |

In one embodiment, the invention provides a topical composition comprising at least one isoxazoline of formula (I) in combination at least one other active agent, and a pharmaceutically acceptable carrier or diluent.

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ectoparasiticidal and/or endoparasiticidal agents.

Veterinary pharmaceutical agents that may be included in the compositions of the invention are well-known in the art (see e.g. *Plumb' Veterinary Drug Handbook*, 5$^{th}$ Edition, ed. Donald C. Plumb, Blackwell Publishing, (2005) or *The Merck Veterinary Manual*, 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide +/− clidinium bromide, chlorothiazide, chlorpheniramine maleate, chlorpromazine, chlorprop-amide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (OXYGLOBIN®®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, known in the art may be combined with the isoxazoline compounds in the topical compositions of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, Ga.).

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, Ga.).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In preferred embodiment of the invention, the invention comprises a topical composition comprising an isoxazoline compound in combination with a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

In a particularly preferred embodiment, the compositions of the invention comprise an isoxazoline compound of formula (I) in combination with methoprene or pyriproxyfen and a pharmaceutically acceptable carrier. It has been surprisingly found that compositions comprising an isoxazoline compound of formula (I) in combination with methoprene or pyriproxyphen exhibit superior long lasting efficacy that is not predictable based on the activity of each active alone.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, novaluron, 1-(2,6-difluorobenzoyl)-3-(2-fluoro-4-(trifluoromethyl)phenylurea, 1-(2,6-difluorobenzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates including, but are not limited to, benomyl, carbanolate, carbaryl, carbofuran, meththiocarb, metolcarb, promacyl, propoxur, aldicarb, butocarboxim, oxamyl, thiocarboxime and thiofanox.

In some embodiments, the compositions of the invention may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine and piperazine as the neutral compound or in various salt forms, diethylcarbamazine, phenols such as disophenol, arsenicals such as arsenamide, ethanolamines such as bephenium, thenium closylate and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophosethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a (4H)-dibenzofurancarboxaldehyde (MGK-11), 2-(2-ethylhexyl)-3a,4,7,7a-tetrahydro-4,7-methano-1H-isoindole-1,3 (2H)dione (MGK-264), dipropyl-2,5-pyridinedicarboxylate (MGK-326) and 2-(octylthio)ethanol (MGK-874).

In a particularly preferred embodiment, the topical compositions of the invention will include permethrin in combination with the isoxazoline active agent.

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

In another embodiment, the compositions of the invention may comprise an active agent from the neonicotinoid class of pesticides. The neonicotinoids bind and inhibit insect specific nicotinic acetylcholine receptors. In one embodiment, the neonicotinoid insecticidal agent that can be combined with an isoxazoline compound to form a topical composition of the invention is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health. Agents of this class are described, for example, in U.S. Pat. No. 4,742,060 or in EP 0 892 060.

In another embodiment, the topical compositions of the invention may comprise nitenpyram, another active agent of the neonicotinoid class of pesticides. Nitenpyram has the following chemical structure and is the active ingredient in the oral product CAPSTAR™ Tablets sold by Novartis Animal Health.

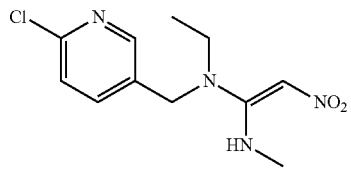 [SMILES: CCN(Cc1ccc(Cl)nc1)/C(=C/[N+](=O)[O-])NC]

Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day. However, nitenpyram is only known to be effective when administered orally as a systemic parasiticide, as with CAPSTAR™ Tablets. Therefore, it is surprising and unexpected that the topical compositions of the invention comprising a combination of nitenpyram with an isoxazoline active agent exhibit the very fast onset of action of nitenpyram because this active agent is not known to be active when administered topically. The topical compositions of the invention comprising a combination of a long-lasting isoxazoline active agent with a very fast acting active agent such as the neonicotinoid active agent nitenpyram provide optimal speed of onset and long lasting activity against ectoparasites.

Nitenpyram has a very low log octanol-water partition coefficient of −0.64 and a relatively high solubility in water of 840 g/L at 20° C. and pH of 7 (see *Supplement to Compendium on Continuing Education for the practicing veterinarian*, vol. 23, no. 3(a), march 2001), indicating that it is not a likely candidate for topical delivery. Based on the very low log p of nitenpyram and the very high water solubility, one of skill in the art would have a very high level of skepticism that this active agent could be effectively delivered in a topical composition. The effectiveness of topical compositions of the invention that comprise nitenpyram are all the more unexpected in view of the physicochemical properties of the compound.

In another preferred embodiment of the invention, topical compositions comprising at least one isoxazoline compound in combination with an IGR and a neonicotinoid active agent are provided. In still another preferred embodiment, the invention provides topical compositions comprising an isoxazoline compound of Formula (I) together with an IGR that mimics juvenile hormone and nitenpyram. In yet another preferred embodiment, the invention provides topical spot-on or pour-on compositions comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound A) in combination with (S)-methoprene or pyriproxyfen and nitenpyram.

In another embodiment, the topical compositions of the invention provide topical spot-on or pour-on compositions that comprise 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound A) in combination with nitenpyram, (S)-methoprene or pyriproxyfen and an avermectin or milbemycin compound. In yet another embodiment of the invention, topical compositions are provided that comprise 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound A) in combination with nitenpyram and/or (S)-methoprene or pyriproxyfen and/or an avermectin or milbemycin compound and/or praziquantel. In this embodiment, the presence of an avermectin or milbemycin compound and/or praziquantel provides potent activity against endoparasites in addition to activity against ectoparasites.

In certain embodiments, an insecticidal agent that can be combined with the compositions of the invention is a semicarbazone, such as metaflumizone.

In another embodiment, the compositions of the invention may advantageously include a combination of isoxazoline compounds known in the art. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelmintic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the compositions of the invention. These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964,621, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. No.

5,703,078 and U.S. Pat. No. 5,750,695, all of which are hereby incorporated by reference in their entirety.

In general, the additional active agent is included in the composition in an amount of between about 0.1 μg and about 1000 mg. More typically, the additional active agent may be included in an amount of about 10 μg to about 500 mg, about 1 mg to about 300 mg, about 10 mg to about 200 mg or about 10 mg to about 100 mg.

In other embodiments of the invention, the additional active agent may be included in the composition to deliver a dose of about 5 g/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 g/kg to about 200 g/kg or about 0.1 mg/kg to about 1 mg/kg of weight of animal. In still another embodiment of the invention, the additional active agent is included in a dose between about 0.5 mg/kg to about 50 mg/kg.

The topical compositions of the invention, which include at least an isoxazoline active agent and a pharmaceutically acceptable carrier that is suitable for topical application to an animal, have been surprisingly discovered to be stable and effective against a broad spectrum of ectoparasites for an extended period of time.

In a preferred embodiment of the inventive compositions, the topical composition will be in the form of a liquid solution or suspension that comprises a pharmaceutically acceptable carrier or diluent that is suitable for application to the skin of an animal. Topical, dermal and subdermal formulations can include emulsions, creams, ointments, gels, pastes, powders, shampoos, pour-on formulations, ready-to-use formulations, spot-on solutions and suspensions.

In a preferred embodiment of the invention, topical compositions suitable for topical administration to a localized area of an animal are provided, including compositions in the form of spot-on or pour-on compositions. In another embodiment, the topical compositions will be in the form of a spray formulation, an aerosol or a foam formulation suitable for administration to an animal. In some embodiments, the liquid solution or suspension formulations comprising isoxazoline active agents will be in a form that can be sprayed on via a metered dose pump or a metered dose aerosol.

Isoxazoline active agents, such as those of Formula (I), are systemically active such that the ectoparasite is affected when taking a blood meal from the host. Accordingly, a minimum concentration of the compounds in the systemic circulation of the animal is required. However, in some situations the isoxazoline active agent may also be active by contacting the parasite on the surface of the animal. Thus, in some embodiments, topical application of the inventive compositions can allow for the active agents to be delivered and distributed throughout the hair coat topically and/or may also provide distribution of the active agent via the sebaceous glands of the animals. When the compound is distributed throughout sebaceous glands, the sebaceous glands can act as a reservoir, whereby there can be a long-lasting effect, e.g. at least one month or longer. For example, Cochet and co-workers reported the distribution of fipronil, a 1-arylpyrazole compound, to the stratum corneum, the viable epidermis and the sebaceous glands and epithelial layers of beagle dogs after spot-on administration (see Cochet et al., *Eur. J. Drug Metab. Pharmacokinet.*, 1997, 22(3), 211-216). Using $^{14}$C radiolabeled drug, the publication demonstrated that fipronil is displaced from the point of application and distributed to the whole skin, where it was persistently detected for up to 56 days after treatment.

Topical application of the inventive compositions enables effective delivery of the active agent transdermally through the skin into the systemic circulation at a concentration sufficient to provide excellent efficacy against ectoparasites. In another preferred embodiment, the compositions of the invention achieve distribution of the active agent both topically over the hair coat of the animal and also transdermally into the blood stream. In this embodiment, the topical compositions provide a high level of efficacy at unexpectedly low plasma concentrations of the isoxazoline active agent.

The outer layer of the epidermis, the stratum corneum, forms the major barrier to both the egress of water and the ingress of xenobiotics into the circulatory system. It is a unique membrane comprised of dead thin flat cells, corneocytes, which are filled with dense keratin, between which is a lipid-rich layer comprised of numerous lipid bilayers. The general consensus is that most xenobiotics pass through the lipid-rich layer between the flat cells. Delivering an active through the skin presents a significant challenge, given the role of the skin as a barrier for keeping foreign substances out. In order for an active ingredient to pass through the stratum corneum, it must pass sequentially across bilayers and therefore cross many hydrophilic-lipophilic interfaces. Because of the efficient barrier of the skin, transdermal delivery is only typically appropriate for potent compounds that require only a small dosage.

Only materials which have good solubility properties in both oils and water will be able to effectively pass across the skin with relative ease. One of the major problems in treating the skin or using the skin to deliver a substance into the systemic circulation arises from the requirement that the active has to possess the correct physicochemical properties to allow it to reach the site of action or circulation. If it is extremely hydrophilic it will reside on the skin surface. If it is extremely lipophilic it will pass into the lipid-rich layer between the cells and will have difficulty penetrating deeper. Only compounds that are small, have balanced solubility in oils and water and a log (octanol-water partition coefficient) of ~2 (log P) will pass through the stratum corneum and into the systemic circulation to any significant degree (see Kenneth B. Sloan (ed.) (1992) Prodrugs: Topical and Ocular Drug Delivery, p. 6, Marcel Dekker, New York). Examples include nicotine and nitroglycerin (GTN). However even these are not absorbed to a large degree. Thus, many compounds are not suitable for transdermal delivery because of their inherent physicochemical properties.

It will be understood that the ability of an active agent to be distributed either topically or transdermally is dependent both on the physicochemical characteristics of the compound and also on the non-active excipients of the formulation, which may induce penetration of the active agent into the skin. While there is no general method to deliver any active agent either topically over the hair coat of an animal or transdermally to an animal, some techniques for enhancing the penetration of active agents into the skin of animals are known. Substances termed "permeation enhancers," are typically used in compositions designed to deliver drugs transdermally to increase the amount of the active that is delivered into the systemic circulation. Permeation enhancers constitute various classes of compounds including certain solvents such as dimethylsulfoxide (DMSO), pyrrolidones, ethanol, propylene glycol, ethyl acetate, dimethylacetamide, and others that are capable of disrupting the barrier function of the stratum corneum. Other substances have also been shown to increase the flux of certain active agents through the skin. These include lipophilic compounds such as laurocapram (Azone); fatty acids or alcohols such as oleic acid, oleyl alcohol, linoleic acid and the like; certain fatty acid esters such as isopropyl myristate, methyl noanoate, methyl caprate and others. Mixtures of certain permeation enhancers with propylene glycol are also known to improve the delivery of certain active ingredients. For example, see Pharmaceutical Skin Penetration Enhancement edited by Kenneth A. Walters and Jonathan Hadgraft, Marcel Dekker, Inc. New York, 1993; ISBN 0-8247-9017-0.

In some embodiments of the invention, the compositions are formulated to control the rate of permeation of the isoxazoline compound in order to maintain efficacious levels of the active in the plasma for a prolonged period of time and significantly extend the duration of efficacy. Thus, in one embodiment, the topical compositions of the invention are formulated with a carrier system that induces the containment of the isoxazoline active agent(s) within the skin to achieve a reservoir effect and controls the permeation rate of the compound into the systemic circulation over a longer period of time. In this manner, the invention provides topical compositions that exhibit surprising long lasting efficacy against ectoparasites. It must be noted that this approach is only applicable to potent active agents that may achieve the desired parasiticidal efficacy with low plasma concentrations, since less potent compounds would not be able to establish an efficacious concentration.

It has been found that the topical compositions of the present invention comprising an isoxazoline active agent in a carrier comprising a lipophilic solvent or lipophilic solvent system result in superb efficacy against ectoparasites for an extended duration of time. Although not wishing to be bound by theory, it is believed that non-active excipients in certain topical formulations of the invention promote the containment of the isoxazoline active agent within the skin for longer periods of time while allowing the active agent to constantly diffuse into the circulatory system at a rate that provides the required concentration of the active in the blood stream to be efficacious against ectoparasites for a longer period of time. This is contrary to the approaches used with typical topical formulations that are designed to enhance the passage of active agents through the skin of an animal into the systemic circulation quickly to obtain the desired biological effect. Thus, in one embodiment the present invention utilizes non-active excipients that discourage the fast permeation of isoxazoline active agents into the systemic circulation.

In one embodiment, the invention provides topical compositions comprising an isoxazoline active agent in a pharmaceutically acceptable carrier wherein the carrier does not include a compound that enhances the permeation of the isoxazoline active agent. In another embodiment, the invention provides topical compositions comprising an isoxazoline active agent and a pharmaceutically acceptable carrier wherein the carrier comprises a solvent or solvent system that promotes the containment of the isoxazoline active agent in the skin of the animal for a longer period of time.

In one embodiment of the invention comprising a carrier that extends the duration of efficacy of the topical compositions, the carrier may comprise a solvent selected from carboxylic acid esters, diesters of dicarboxylic acids, fatty acid esters or diesters of fatty diacids, or a combination thereof, including, but not limited to, isopropyl palmitate, isostearyl lactate, diisopropyl adipate, dibutyl adipate, diethyl sebacate, dibutyl sebacate, octyl palmitate, polyethyleneglycol (PEG) stearate and cetearyl octanoate; oils including, but not limited to, mineral oil, diglycerides, triglycerides, jojoba oil, lecithin and castor oil, or a combination thereof; long chain aliphatic alcohols such as isostearyl alcohol and the like; fatty alcohols and their esters, including for example, cetyl alcohol, cetearyl alcohol and the like, or a combination thereof; polyethylene glycols of different molecular weight ranges including, but not limited to, PEG 300, PEG 400, PEG 600 and PEG 1000, or a combination thereof; and glycol ethers including, but not limited to, diethyleneglycol monoethyl ether (Transcutol®), butyl diglycol, propylene glycol monomethyl ether, propylene glycol monoethyl ether, dipropylene glycol n-butyl ether, ethylene glycol monoethyl ether, ethylene glycol monomethyl ether and dipropylene glycol monomethyl ether, or a combination thereof; or a combination of two or more of these solvents.

Excipients that may also promote the containment of the active agent in the skin for longer periods of time and may be included in the compositions of the invention include, but are not limited to, mixed esters of sucrose and carboxylic acids including sucrose acetate isobutyrate (SAIB) and the like; low-temperature melting waxes, hydrogenated vegetable oils, caprylic/capric glycerides; glycerol esters, including for example, triacetin, glycerol monooleate, glycerol monolinoleate, glycerol stearate, glyceryl distearate and the like; triglycerides, including for example, caprylic, capric/myristic/stearic triglyceride; thermoreversible polymers, such as Pluronic and poloxamers, including for example, Lutrol F127 by itself or in mixture with other poloxamers; or a combination thereof.

In another embodiment of the invention the pharmaceutically acceptable carrier for the topical compositions comprise a mixture of a diester of a dicarboxylic acid alone or in combination with one or more of additional solvents listed above, and/or an "oily" lipophilic substance, including a liquid or low melting lipophilic active agent such as (S)-methoprene, pyriproxyfen and/or permethrin; and/or a mixed ester of sucrose and carboxylic acids including a mixed ester of sucrose and acetic and isobutyric acids such as sucrose acetate isobutyrate (SAIB), and/or low melting waxes and/or hard fats.

Although not wishing to be bound by theory, the inclusion of certain lipophilic solvents in the topical compositions of the invention promote the residence time of the isoxazoline active agent within the skin while allowing an effective concentration of the active agent to pass slowly into the circulatory system to achieve the desired efficacy for longer periods of time.

In a preferred embodiment, the diester of a dicarboxylic acid is diethyl sebacate or diisopropyl adipate. In another embodiment, the blend of solvents comprising a dicarboxylic acid ester comprises a glycol or polyglycol, or a glycol or polyglycol ether or ester including, but not limited to, ethylene glycol (EG), propylene glycol (PG), liquid polyoxyethylene glycols (PEGs) of various grades including PEG 400, EG or PG monocaprylate, EG or PG caprylate, EG or PG monolaurate, EG or PG dicaprylate/dicaprate, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like, or a combination thereof; an ether including, but not limited to, dimethyl isosorbide; an ester or diester including, but not limited to, triacetin, lauryl lactate; and other solvents including glycerol formal, or mixtures thereof.

In preferred embodiments, the carrier for the topical compositions comprises a dialkyl ester of a dicarboxylic acid such as diethyl sebacate, diisopropyl sebacate, diisopropyl adipate, dibutyl adipate, or a combination thereof, alone or in combination with solvents selected from:
- a) a propylene glycol (PG) ester including PG monocaprylate, PG caprylate, PG monolaurate, PG dicaprylate/dicaprate, or a combination thereof;
- b) an ether solvent including dimethyl isosorbide, diethylene glycol monoethyl ether (also known as DGME or Transcutol®), or a combination thereof;
- c) a carboxylic acid ester including, but not limited to, triacetin, lauryl lactate, isopropyl palmitate, diisopropyl sebacate, or a combination thereof; and
- d) other "oily" or lipophilic organic solvents including glycerol formal and the like.

In some embodiments, the amount the additional solvents combined with the carboxylic acid ester or diester of a dicarboxylic acid are present in an amount of at least about 1% (v/v), at least about 5% (v/v), at least about 9.0% (v/v), at least about 13% (v/v), at least about 17% (v/v) or at least about 20% (v/v). Preferably the additional solvents will be in an amount of at least about 9% (v/v).

In other embodiments, the additional solvents will be present in an amount of about 5-70% (v/v), about 10-60% (v/v), about 10-50% (v/v), about 15-60% (v/v) or about 15-50% (v/v). In preferred embodiments, the additional solvents will be present in an amount of about 20-70% (v/v), about 20-60% (v/v), about 20-50% (v/v) or about 25-50% (v/v).

The pharmaceutically acceptable carrier may include suitable carriers or diluents commonly used in the formulation art including aqueous or organic solvents or mixtures of solvents. These organic solvents may be found, for example, in Remington Pharmaceutical Sciences, 21$^{st}$ Edition (2005). Other solvents and/or additives that may be used in the topical compositions include, but are not limited to, PEG ethers and PEG esters including, but not limited to, PEG esters of carboxylic acids and dicarboxylic acids and PEG esters of fatty acids, glycerol esters including triacetin, caprylic/capric triglycerides (Miglyol 812®) and the like; glycerol ethers including glycerol formal; propylene glycol dicaprylate/dicaprate (Miglyol 840®), lauryl lactate, triacetin, diisopropyl adipate (DIPA, also known as CERAPHYL 230), diisobutyl adipate, dimethyl isosorbide (DMI), acetyltributyl citrate, oleic acid; carboxylic acid esters including esters of diacids, ketones including acetone, methylisobutyl ketone (MIK), methyl ethyl ketone, and the like; acetonitrile, $C_1$-$C_{12}$ alcohols including benzyl alcohol, methanol, ethyl alcohol, isopropanol, and butanol; aromatic ethers such as anisole; amides including dimethylacetamide, monomethylacetamide and dimethylformamide; dimethyl sulfoxide (DMSO), ethylene glycol, propylene glycol, a glycol carbonate including, but not limited to, propylene carbonate and, butylene carbonate; 2-pyrrolidone, N-methylpyrrolidone, $C_1$-$C_{12}$ alkyl esters of carboxylic acids including butyl or octyl acetate and benzyl acetate; $C_1$-$C_{12}$ alkyl esters of dicarboxylic acids; aryl esters including benzyl benzoate, ethyl benzoate and the like; and diethyl phthalate, or a mixture of at least two of these solvents.

However, in one embodiment, the invention provides topical compositions comprising at least one isoxazoline active agent, optionally in combination with one or more additional active agents, in a pharmaceutically acceptable carrier, wherein the carrier does not comprise glycofurol. In another embodiment, the pharmaceutically acceptable carrier of the topical compositions does not comprise a binary mixture of propylene glycol and glycerol formal.

As vehicle or diluent, mention may also be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons including limonene or alternatively, for example, medium-chain (such as $C_8$ to $C_{12}$) triglycerides, or mixtures thereof.

In one embodiment, solvents and/or additives that control the permeation rate of the active may be added to a composition comprising one of the formulation carriers described herein, including carriers comprising a dialkyl ester of a dicarboxylic acid such as diethyl sebacate or the like. In another embodiment, solvents and/or additives that control the permeation rate of the active may be added to carriers comprising other solvents described herein or may be used alone in the composition.

It will be appreciated by those skilled in the art that the skin of different animals will be different in nature and may be more or less permeable to the isoxazoline active agent. For example, the retainment of the isoxazoline active agent on the skin of a cat may be more difficult than dogs. Accordingly, in some situations with certain animals the topical compositions of the invention will utilize solvents that enhance the permeation of the isoxazoline active agent through the skin of the animal rather than solvents and excipients that retain the active agent on the skin of the animal for longer periods of time. Thus, in another embodiment of the invention, topical compositions are provided that include solvents that enhance the permeation of isoxazoline active agents through the skin of the animal. These solvents provide a greater proportion of the active agent through the skin and thereby improve the efficacy and duration of time. In this embodiment, the permeation enhancing solvent permits a greater proportion of the isoxazoline active agent through the skin into the systemic circulation. It will be appreciated by those of skill in the art that this effect allows a greater level of efficacy at lower doses of the active. Selected solvents that enhance the permeation of the isoxazoline active agent include, but are not limited to, dimethyl isosorbide; and glycol ethers including, but not limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like. Other solvents that enhance the permeation of the isoxazoline active agent described below may also be used in the compositions.

In one embodiment of the invention, the pharmaceutically acceptable carrier of the formulation may comprise $C_8$-$C_{20}$ long-chain aliphatic alcohols or esters thereof. In another embodiment, the carrier comprises $C_1$-$C_{12}$ alcohols or esters thereof, $C_1$-$C_4$ alcohols or esters thereof or $C_3$-$C_8$ alcohols or esters thereof. In some embodiments, the esters formed with the alcohol include esters of $C_1$-$C_{12}$ carboxylic acids or diacids, or esters of $C_6$-$C_{16}$ carboxylic acids or diacids. Esters include, but are not limited to, acetates such as ethyl acetate and the like; and esters of $C_1$-$C_{12}$ alcohols and a dicarboxylic acid or a hydroxy-substituted carboxylic acids.

In another embodiment, the pharmaceutically acceptable carrier comprises $C_4$-$C_{22}$ fatty acids or esters thereof, including esters with $C_6$-$C_{20}$ long chain alcohols, $C_1$-$C_{12}$ alcohols, $C_1$-$C_4$ alcohols or $C_3$-$C_8$ alcohols; $C_{10}$-$C_{18}$ saturated fatty acids or esters thereof, including esters with $C_6$-$C_{20}$ long chain alcohols, $C_1$-$C_{12}$ alcohols, $C_1$-$C_4$ alcohols or $C_3$-$C_8$ alcohols; $C_{10}$-$C_{18}$ unsaturated fatty acids or esters thereof, including esters with $C_6$-$C_{20}$ long chain alcohols, $C_1$-$C_{12}$ alcohols, $C_1$-$C_4$ alcohols or $C_3$-$C_8$ alcohols; monoesters or diesters of $C_6$-$C_{16}$ aliphatic carboxylic acids and carboxylic diacids, including esters with $C_6$-$C_{20}$ long chain alcohols, $C_1$-$C_{12}$ alcohols, $C_1$-$C_4$ alcohols or $C_3$-$C_8$ alcohols, or mixtures thereof. In other embodiments, the carrier may include $C_1$-$C_{10}$, $C_1$-$C_8$ or $C_1$-$C_6$ alcohols or esters thereof.

In another embodiment, the compositions of the invention comprise aromatic alcohols or esters thereof. In one preferred embodiment, the topical compositions of the invention may include benzyl alcohol as a solvent.

In another embodiment, preferred solvents include $C_1$-$C_{12}$ alkyl esters of carboxylic acids such as butyl acetate, octyl acetate, lauryl lactate or isopropyl palmitate, and $C_1$-$C_{12}$ alkyl esters of dicarboxylic acids, including diisopropyl adipate, diethyl sebacate and diisopropyl sebacate. In other embodiments, the carrier may include $C_1$-$C_{10}$, $C_1$-$C_8$ or $C_1$-$C_6$ alkyl esters of carboxylic acids or $C_1$-$C_{10}$, $C_1$-$C_8$ or $C_1$-$C_6$ alkyl diesters or dicarboxylic acids. In one embodiment, the carboxylic acid or dicarboxylic acid is a $C_4$-$C_{22}$ fatty acid or dicarboxylic acid. In another embodiment, the carboxylic acid or dicarboxylic acid is a $C_1$-$C_{12}$ carboxylic acid or dicarboxylic acid. In other embodiments, the carboxylic acid or dicarboxylic acid is a $C_1$-$C_{10}$, $C_1$-$C_8$ or $C_1$-$C_6$ carboxylic acid or dicarboxylic acid.

In some preferred embodiments, the carrier or diluent include a derivative of glycerol including, but not limited to, glycerol monoesters (e.g. monoglycerides), glycerol diesters (e.g. diglycerides), glycerol triesters (e.g. triglycerides such as triacetin), or glycerol formal, or mixtures thereof. Glycerol formal is a mixture of 5-hydroxy-1,3-dioxane and 4-hydroxymethyl-1,3-dioxolane (approximately 60:40), which are cyclic ether compounds derived from glycerol and having 2 oxygen atoms in the ring structure and substituted by alcohol group. Glycerol Formal is a low odor and low toxic solvent for a wide variety of applications in pharmaceutical and cosmetics industry including anti-parasite veterinary formulations.

In another embodiment of the invention, the organic solvents may comprise diisopropyl adipate, dipropylene glycol monomethyl ether, propylene glycol monomethyl ether, 2-pyrrolidone, N-methylpyrrolidone, diethylene glycol monoethyl ether, triacetin, butyl acetate, benzyl alcohol, octyl acetate, propylene carbonate, oleic acid, or a mixture of at least two of these solvents.

In some embodiments of the invention, the carrier comprises dimethyl isosorbide. Dimethyl isosorbide (DMI) is a high purity solvent and carrier which offers a safe, effective delivery enhancement mechanism for active ingredients in personal care products and pharmaceutical formulations. In addition dimethyl isosorbide is sometimes used as an epidermal penetration enhancer to provide enhanced penetration of active agents to the epidermis. It may also provide delivery of active agents into the skin while avoiding crystallization of the active agent, which will severely limit the effectiveness of the formulation. Dimethyl Isosorbide is soluble in a variety of ingredients including water, cottonseed oil, isopropanol, isopropyl myristate, propylene glycol, polysorbate 20, and polysorbate 80.

In other embodiments, the carrier or diluent may comprise a glycol derivative including, but not limited to, propylene glycol, ethylene glycol; glycol ethers and polyglycol ethers including, but not limited to, butyl diglycol, propylene glycol monomethyl ether, propylene glycol monoethyl ether, dipropylene glycol n-butyl ether, ethylene glycol monoethyl ether, ethylene glycol monomethyl ether, dipropylene glycol monomethyl ether, and diethylene glycol monoethyl ether (DGME or Transcutol®).

In a preferred embodiment, the topical compositions of the invention comprising isoxazoline active agent(s) are dissolved in a pharmaceutically acceptable carrier comprising one or more solvents. In some embodiments of the invention solvents include, but are not limited to, dimethyl isosorbide (DMI), glycerol formal (methylidinoglycerol or glycerin formal), triacetin, liquid polyethyleneglycols including PEG 400, diisopropyl adipate (DIPA), isopropyl palmitate, silicone fluid including SILICONE FLUID 200 and Silicone Fluid 1 cst and/or Silicone Fluid 2 cst and the like; propylene glycol (or other aliphatic dihydric alcohols), benzyl alcohol, propylene glycol esters including propylene glycol dicaprylate/dicaprate, propylene carbonate, propylene glycol monocaprylate, propylene glycol dicaprylate, propylene glycol monolaurate and propylene glycol dilaurate; alkyl esters of dicarboxylic acids including diethyl sebacate (DES), diisopropyl sebacate; and esters or diesters of fatty acid, or combinations thereof.

In an embodiment of the invention, the compositions of the invention may include surfactants. The surfactants may be anionic, cationic, non-ionic or amphoteric surfactants. Anionic surfactants include, but are not limited to, alkaline stearates; calcium stearate; triethanolamine stearate; sodium abietate; alkyl sulfates; sodium dodecylbenzenesulphonate, sodium dioctylsulphosuccinate; fatty acids, and the like. Examples of cationic surfactant include, but are not limited to, water-soluble quaternary ammonium salts of formula; cetyltrimethylammonium bromide and octadecylamine hydrochloride. Non-ionic surfactants that may be used in the compositions include, but are not limited to, polyoxyethylenated (PEGylated) esters including, but not limited to, sorbitan esters and fatty acid esters; polyethylene glycol stearate, polyoxyethylenated derivatives of castor oil, polyglycerol esters, polyoxyethylenated fatty alcohols, polyoxyethylenated fatty acids, and copolymers of ethylene oxide and propylene oxide including, but not limited to, block co-polymers of ethylene oxide and propylene oxide such as poloxamers and the like (e.g. Lutrol® F grades and L grades from BASF including Lutrol® F68, F87, F 108 and F 127 and others), and the like. Further example of surfactants include, but are not limited to, CAPRYOL™ 90 (propylene glycol monocaprylate), CAPRYOL™ PGMC (propylene glycol monocaprylate) which are oily liquids having an HLB (hydrophilic-lipophilic balance) of 6 and 5, respectively. Topically they can be used as a co-surfactant in microemulsions and as a solubilizer/penetration enhancer.

As used herein, HLB values have the following general meanings: compounds with a HLB value of <10 tend to be lipid soluble (water insoluble) and solvents with a HLB >10 tend to be water soluble. Surfactants having HLB between 4 and 8 are typically useful as anti-foaming agents. Surfactants having HLB from 7 to 11 may be useful as W/O (water in oil) emulsifiers. HLB of 12 to 16 typically indicates a surfactant may be useful in oil in water emulsions, and HLB of 11 to 14 is indicative of a wetting agent. HLB of 12 to 15 is typical of detergents, and HLB of 16 to 20 indicates a solubilizer or hydrotrope. There is significant an overlap of ranges/uses, and a skilled person well understands that the HLB value alone cannot be used to predict whether a particular surfactant will serve a specific purpose (e.g. anti-foaming agent, emulsifier, wetting agent, solubilizer, hydrotrope). Therefore, in general, determination of a suitable system of solvent, active agent, surfactant(s) and other excipients necessarily involves non-routine experimentation and inventive effort.

The compositions may also include surfactants such as oleoyl macrogolglycerides (polyoxylglycerides, for example, LABRAFIL® M1944CS and LABRAFIL® M2125CS both having an HLB of 4). These compounds may also be used, for example, as oily phase for emulsions, microemulsions, and as penetration enhancers.

In another embodiment, the polyoxylglycerides may include polyethyleneglycol caprylic/caprylic glycerides such as LABRASOL® (HLB of 14. Topically it is used as a surfactant in microemulsions, and can also act as a solubility/penetration enhancer in topical formulations.

In another embodiment the surfactant is LAUROGLYCOL™90 (propylene glycol monolaurate) having an HLB of 5. It is a co-surfactant for microemulsions in topical formulations and can also act as a solubilizer/penetration enhancer in topical formulations. In some embodiments, the surfactant is PLUROL® OLEIQUE CC497 (polyglyceryl oleate), having an HLB of 6.

Certain solvents suitable for topical formulations may be characterized as having good spreading properties while other solvents for topical formulations may be characterized by an ability to enhance permeation of active agents through the skin barrier into the systemic circulation (see for example, *Pharmaceutical Skin Penetration Enhancement*, edited by Jonathan Hadgraft and Kenneth A. Walters, Marcel Dekker, Inc. New York 1993). In some instances, solvents suitable for topical formulations may include both good spreading and good permeation characteristics. DIPA, diisopropyl sebacate, DES and Miglyol 840 have both good spreading and permeation characteristics. Transcutol, DMI, lauryl lactate, propylene glycol caprylate, propylene glycol monocaprylate and propylene glycol monolaurate have good permeation enhancing properties but are not considered to have particularly good spreading properties. In certain embodiments of the invention, the compositions will comprise mixtures of solvents that will enhance the spreading ability and/or the permeation enhancing ability of the composition.

In some embodiments of the invention, formulations are provided wherein the carrier comprises solvents that exhibit both good spreading and permeation characteristics including, but not limited to, DIPA, diisopropyl sebacate, DES and Miglyol® 840. In other embodiments, the invention provides formulations wherein the carrier comprises solvents that exhibit good spreading characteristics. In still another embodiment of the invention, formulations are provided wherein the carrier vehicle comprises solvents that enhance the permeation of the active agent through the skin into the systemic circulation.

In one embodiment, the composition exhibits long lasting efficacy and provides protection against parasites in domestic animals for at least one month. In one embodiment, the composition comprises a carrier that includes a solvent system comprised of a carboxylic acid alkyl ester or diester of a dicarboxylic acid. In another embodiment, the composition comprises a blend of solvents comprising a carboxylic acid alkyl ester or a diester of a dicarboxylic acid.

In another embodiment, the compositions of the invention exhibit very long lasting efficacy of at least 90% against fleas and/or ticks that for a period of at least 1 month, at least 2 months, at least 3 months, at least 4 months, at least 5 months, or at least 6 months against fleas and/or ticks. In one embodiment, the long-lasting composition comprises a carrier that includes a carboxylic acid alkyl ester or a diester of a dicarboxylic acid, including diethyl sebacate and diisopropyl adipate. In another embodiment, the long-lasting composition comprises a carboxylic acid alkyl ester or a diester of a dicarboxylic acid combined with an co-solvent including, but not limited to, a propylene glycol (PG) ester including PG monocaprylate, PG caprylate, PG monolaurate and PG dicaprylate/dicaprate; diethyleneglycol monoethyl ether (DGME, Transcutol®), mineral oil, triglycerides, diglycerides, isostearyl alcohol, isostearyl lactate, dibutyl adipate, dibutyl sebacate; polyethylene glycols (PEGs) including PEG 400, PEG stearate; lecithin, castor oil and castor oil derivatives, film formers, myristyl myristate, dimethiconol argenine, sucrose acetyl isobutyrate, and the like, or a combination thereof.

In still another embodiment, the long-lasting compositions that provide an efficacy of at least 90% against fleas and/or ticks for at least 1 month, at least 2 months, at least 3 months, at least 4 months, at least 5 months, or at least 6 months, comprise a carrier vehicle that includes dimethyl isosorbide. As mentioned above, DMI is a known permeation enhancer, and use of this solvent in some topical formulations of the invention results in increased delivery of the active agent into the systemic circulation. In particular, it was found that the use of DMI in topical formulations for cats resulted in surprising efficacy for up to at least 3 months, at least 4 months, at least 5 months or even at least 6 months, against fleas.

In yet another embodiment, the long-lasting compositions that provide an efficacy of at least 90% against fleas and/or ticks comprises a glycol ether including, but not limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like.

As discussed above, isoxazoline active agents such as those of Formula (I), and in particular 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound A), are systemically active such that the ectoparasite is affected when taking a blood meal from the host. Accordingly, a minimum concentration of the compounds in the systemic circulation of the animal is required to effectively control ectoparasites such as ticks and fleas. It was surprisingly found that the topical formulations of the invention comprising an isoxazoline active agent provide excellent efficacy against fleas and ticks at unexpectedly very low plasma concentrations. In some embodiments, the topical compositions of the invention comprising selected solvents and excipients, including dialkyl esters of dicarboxylic acids such as diethyl sebacate and the like, result in constant low levels of the active agent over a prolonged period of time. In some embodiments, the concentration of the active agent in the plasma that is sufficient to obtain at least 90% efficacy against fleas and/or ticks is less than or equal to about 200 ng/mL or less than or equal to about 150 ng/mL. In other preferred embodiments, the concentration of the isoxazoline active agent in the plasma required to attain 90% efficacy against fleas and/or ticks is less than or equal to about 100 ng/mL, less than or equal to about 75 ng/mL or even less than or equal to about 50 ng/mL. In other embodiments of the invention, the concentration of the isoxazoline active agent in the plasma required to attain 90% efficacy against fleas and ticks is about 75-100 ng/mL, about 50-75 ng/mL or about 30-50 ng/mL.

Furthermore, it was also surprisingly found that the concentration of the isoxazoline active agent (Compound A) in the plasma required to attain an efficacy of at least 90% against certain tick species compared to an untreated control or a control group treated with a placebo was significantly less than the plasma concentration required to attain 90% efficacy from another mode of administration that achieves high systemic exposure, such as oral or injectable administration. It was found that the concentration of the isoxazoline active agent required to achieve 90% efficacy against the tick species *A. americanum, D. variabilis* and *R. sanguineus* in dogs was about 42%, 36% and 32% lower than the concentration required from oral administration (see Example 13). This effect is surprising and unexpected for an active agent that is active against ectoparasites through ingestion of a blood meal, as with the isoxazoline class of compounds. Although not wanting to be bound by theory, the lower plasma concentration required to achieve 90% efficacy from the topical compositions of the invention may indicate that the compositions provide protection against ectoparasites by acting both topically on the surface of the animal and systemically. The improved efficacy of the topical compositions of the invention against these tick species at significantly lower plasma concentrations may allow for a longer duration of efficacy based on the ability of the non-active excipients in the inventive compositions to provide a slow delivery of effective amounts of isoxazoline active agents into the blood stream from the site of application.

As mentioned above, it was surprisingly discovered that the addition of certain other active agents with the isoxazoline active agent in the topical compositions of the invention significantly enhanced the long lasting efficacy of the compositions. For example, inclusion of an IGR active agent such as the juvenile hormone mimic methoprene in the topical compositions resulted in significantly longer lasting efficacy against ectoparasites. Thus, in one preferred embodiment the invention provides very long lasting topical compositions comprising at least one isoxazoline active agent in combination with an insect growth regulator (IGR) active agent. Preferably, the IGR will be a juvenile hormone mimic including azadirachtin, diofenolan, fenoxycarb, hydroprene, kinoprene, pyriproxyfen, tetrahydroazadirachtin or 4-chloro-2-(2-chloro-2-methylpropyl)-5-(6-iodo-3-pyridylmethoxy)pyridizin-3(2H)-one, as discussed herein. More preferably, the IGR will be methoprene or pyriproxyfen. As described in the non-limiting examples, the inclusion of the IGR (S)-methoprene with the isoxazoline active agent resulted in significantly longer lasting efficacy. This effect is surprising and unexpected, as methoprene is not an adulticide (see Examples 1-3).

In another embodiment of the invention, it was surprisingly discovered that inclusion of a neonicotinoid active agent such as nitenpyram in the topical compositions of the invention significantly increased the speed of kill of the compositions against fleas. Thus, a topical composition comprising nitenpyram in combination with an isoxazoline active agent and optionally an IGR active agent and/or other oily active agents and/or active agents with low melting points such as permethrin, provide efficacy of at least 90% against fleas as early as 12 hours after administration of the topical formulation and also provide long lasting efficacy. In yet other embodiments of the invention, the topical compositions provide efficacy of at least 90% against fleas as early as 9 hours or 6 hours after administration. In one embodiment of the invention, the compositions comprising a combination of nitenpyram and an isoxazoline active agent provide efficacy of at least 90% against fleas as early as 12 hours, 9 hours or 6 hours after treatment and an efficacy of at least 90% for a period of at least 1 month. In other embodiments, the compositions comprising a combination of nitenpyram and an isoxazoline active agent provide efficacy of at least 90% as early as 12 hours, 9 hours or 6 hours after treatment and an efficacy of at least 90% for a period of at least 2 months or at least 3 months, or longer. The fast acting and long lasting protection provided by a combination of the neonicotinoid nitenpyram and an isoxazoline active agent is very surprising and unexpected because nitenpyram is only known to be effective when administered orally, as with the product CAPSTAR™ Tablets.

In other embodiments, the compositions of the invention may be in the form of oil-in-water or water-in-oil emulsions. In some embodiments the oily phase may be a vegetable oil, for example, olive oil or arachis oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan mono oleate, and condensation products of the said partial esters with ethylene oxide, for example, polyoxyethylene sorbitan mono oleate, and the like. In some embodiments, the emulsions may also contain preservatives.

In another embodiment of the formulation, the composition of the invention is in the form of a microemulsion. Microemulsions are well suited as the liquid carrier vehicle. Microemulsions are typically quaternary systems comprising an aqueous phase, an oily phase, a surfactant and a co-surfactant. They are usually translucent and isotropic liquids. Microemulsions are composed of stable dispersions of microdroplets of the aqueous phase in the oily phase or conversely of microdroplets of the oily phase in the aqueous phase. The size of these microdroplets is typically less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides. In another embodiment of the oily phase, the triglycerides are medium-chain triglycerides, for example $C_8$-$C_{10}$ caprylic/capric triglyceride. In another embodiment, the oily phase will represent a % v/v range selected from the group consisting of about 1 to about 20%; about 2 to about 15%; about 7 to about 10%; and about 8 to about 9% v/v of the microemulsion.

The aqueous phase typically includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 10% v/v or about 1 to about 4% v/v in the microemulsion.

Surfactants for the microemulsion typically include diethylene glycol monoethyl ether, dipropyelene glycol monomethyl ether, polyglycolyzed $C_8$-$C_{10}$ glycerides or polyglyceryl-6 dioleate, or a combination of these surfactants. In addition to these surfactants, the co-surfactants include short-chain alcohols, such as ethanol and propanol. Additionally, poloxamers and Pluronic F127 can be used as surfactants.

Some compounds are common to the three components discussed above, i.e., aqueous phase, surfactant and co-surfactant. However, it is well within the skill level of the practitioner to use different compounds for each component of the same formulation.

Oily suspensions may be formulated by suspending the active ingredient in a vegetable oil, for example, arachis oil, olive oil, sesame oil or coconut oil, or in mineral oil such as liquid paraffin, and the like. The oily suspensions may contain a thickening agent, for example, beeswax, hard paraffin or cetyl alcohol, and the like. These compositions may be preserved by the addition of an anti-oxidant such as ascorbic acid or other known preservatives.

Aqueous suspensions may contain the active agents in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol mono-oleate, or condensation products of ethylene oxide, with partial esters derived from fatty acids and hexitol anhydrides, for example polyethylene sorbitan mono-oleate. The aqueous suspensions may also contain one or more preservatives, for example ethyl, or n-propyl, p-hydroxybenzoate, one or more coloring agents.

Colorants may be added to the inventive formulations. Colorants contemplated by the present invention are those commonly known in the art. Specific colorants include, for example, dyes, FD&C Blue #1 Aluminum Lake, caramel, colorant based upon iron oxide or a mixture of any of the foregoing. Especially preferred are organic dyes and titanium dioxide. Preferred ranges include from about 0.01% to about 2% (w/v), more preferably from about 0.01% to about 0.5% (w/v).

In preferred embodiment, the compositions of the invention are in the form of a spot-on formulation that is applied to a localized area on an animal, rather than the entire coat of the animal or a large portion of the animal's coat. In one embodiment of a localized region, the location is between the shoulders. The spot-on formulation according to the present invention provide long-lasting and broad-spectrum efficacy against ectoparasites and/or endoparasites when the solution is applied to the animal. The spot-on formulations provide for topical administration of a concentrated solution, suspension, microemulsion or emulsion for intermittent application to localized area on the animal, generally between the two shoulders.

Spot-on formulations are well known techniques for topically delivering certain antiparasitic agents to a limited area of the host. However, not all compounds are suited for formulation in spot-on formulations because the physico-chemical characteristics of the active agent may not allow effective distribution of the compound topically or transdermally. U.S. Pat. Nos. 5,045,536; 6,395,765; 6,096,329; 7,262,214; 6,426,333; 6,482,425; 6,962,713; 6,998,131; and 7,531,186, all incorporated herein by reference, describe spot-on formulations. WO 01/957715, also incorporated herein by reference, describes a method for controlling ectoparasites in small rodents as well as interrupting or preventing the diseases caused by arthropods in small rodents, which comprise applying topical formulations, such as spot-on compositions, to the skin, or hair of the rodents.

Spot-on formulations may be prepared by dissolving the active ingredients into the pharmaceutically or veterinary acceptable vehicle. Alternatively, the spot-on formulation can be prepared by encapsulation of the active ingredients to leave a film of the therapeutic agent on the surface of the animal. These formulations will vary with regard to the weight of the therapeutic agent in the combination depending on the species of host animal to be treated, the severity and type of infection and the body weight of the host.

For spot-on formulations, the pharmaceutically acceptable carrier may be a liquid carrier vehicle as described herein, and other carriers described in the art, for example in U.S. Pat. No. 6,395,765 and other patents listed in the previous paragraph. In some embodiments, the liquid carrier vehicle can optionally contain a crystallization inhibitor such as the crystallization inhibitors described below, or mixtures thereof, to inhibit the formation of crystals or precipitate of the active components.

The veterinarily acceptable carrier will generally comprise a diluent or vehicle in which the active agents are soluble. It will be apparent to those of skill in the art that the carrier or diluent of the topical compositions must be able to deliver the active agents to the targeted location without the active agents precipitating from solution or forming crystals. In some embodiments, the carrier or diluent of the compositions will be suitable to avoid precipitation or crystallization of the active agents. In other embodiments, the compositions may include a crystallization inhibitor component in addition to the carrier or diluent.

Crystallization inhibitors which are useful for the invention include but are not limited to:

(a) polyvinylpyrrolidone, polyvinyl alcohols, copolymers of vinyl acetate and of vinylpyrrolidone, 2-pyrrolidone including N-methylpyrrolidone, dimethylsulfoxide, polyethylene glycols, co-polymers of polyoxyethylene and polyoxypropylene, benzyl alcohol, mannitol, glycerol, sorbitol or polyoxyethylenated esters of sorbitan; lecithin or sodium carboxymethylcellulose; or acrylic derivatives, such as polymers derived from acrylic monomers including polyacrylates or polymethacrylates; and, a solvent as described herein that inhibits the crystallization of the active agent, and similar compounds;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil);

(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used;

(d) amine salts of formula $N^+HR'R''R'''Y^-$, in which the R radicals are identical or different optionally hydroxylated hydrocarbon radicals and $Y^-$ is the anion of a mineral or organic acid; octadecylamine hydrochloride is one of the cationic surfactants which can be used;

(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil including hydrogenated castor oil and its derivatives, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine; or (g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. Other crystallization inhibitor pairs include a polyethylene glycol and a non-ionic surfactant. Additional crystallization pairs including other mixtures are also contemplated. These agents can be selected from the compounds mentioned above as crystallization inhibitor.

In one embodiment of the film-forming agent, the agents are of the polymeric type which include but are not limited to the various grades of polyvinylpyrrolidone, polyvinyl alcohols, polyethylene glycols and copolymers of vinyl acetate and of vinylpyrrolidone.

In one embodiment of the surface-active agents, the agents include but are not limited to those made of non-ionic surfactants. In another embodiment of the surface active agents, the agent is a polyoxyethylenated ester of sorbitan. In yet another embodiment of the surface-active agent, the agents include the various grades of polysorbate, for example Polysorbate 80 and polyoxyethylenated derivatives of castor oil including hydrogenated castor oil derivatives.

In another embodiment of the invention, the film-forming agent and the surface-active agent can be incorporated in similar or identical amounts within the limit of the total amounts of crystallization inhibitor mentioned above.

In some embodiments, the crystallization inhibitor can be present in a proportion of about 1 to about 30% (w/v). Typically, the crystallization inhibitor may be present in a proportion of about 1% to about 20% (w/v), about 1% to about 10% (w/v), or about 5% to about 15% (w/v). Acceptable inhibitors are those whose addition to the formulation inhibits the formation of crystals of the active agents when the formulation is applied. In some embodiments, formulations may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the isoxazoline active agent in a solvent as described above with 10% (w/v) of the crystallization inhibitor will result in less than 20, preferably less than 10 crystals when placed on a glass slide at 20° C. for 24 hours.

In some embodiments of the invention, an emollient and/or spreading and/or film-forming agent may be added to the topical compositions of the invention. Emollients, spreading agents and film forming agents are well known in the art. In various embodiments, the emollients, spreading agents and film forming agents that may be used in the topical compositions include the components listed in (a) to (g) above, including polymer derivatives such as polyvinylpyrrolidone, polyvinyl alcohols and copolymers of vinyl acetate and vinylpyrrolidone; anionic surfactants; cationic surfactants; non-ionic surfactants; amphoteric surfactants; amine salts, and combinations thereof. In one embodiment, the emollient is used in a proportion of from about 0.1 to about 10%, or about 0.25 to about 5% (w/v).

Optionally, a fragrance may be added to any of the compositions of the invention. Fragrances which are useful for the invention include but are not limited to:

(i) carboxylic acid esters such as octyl acetate, isoamyl acetate, isopropyl acetate and isobutyl acetate;

(ii) fragrant oils such as lavender oil.

The inventive formulations may contain other inert ingredients such as antioxidants, preservatives, or pH stabilizers. These compounds are well known in the formulation art. Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol, tert-butyl hydroquinone (TBHQ), and the like, may be added to the present formulation. The antioxidants are generally added to the formulation in amounts of from about 0.01 to about 2.0%, based upon total weight of the formulation, with about 0.05 to about 1.0% being especially preferred.

Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate.

In other embodiments, the topical compositions of the invention may be in the form of a pour-on formulation. Pour-on formulations are described, for example, in U.S. Pat. No. 6,010,710, which is incorporated herein by reference. Some pour-on formulations are advantageously oily, and generally comprise a diluent or vehicle and also a solvent (e.g. an organic solvent) for the active ingredient if the latter is not soluble in the diluent. Other pour-on formulations may be in hydrophilic carriers, including in alcohol, glycol or glycol ether based carriers. Pour-on formulations are typically administered to livestock animals such as cattle and sheep. Typically, pour-on formulations are administered to the animal as a stripe to an external surface of the animal, e.g. a stripe from head to tail of the animal. In one embodiment, the process comprises applying the solution to livestock animals before they arrive in the Feed Lot, it being possible for this application to be the final one before the animals are slaughtered.

Typically, the isoxazoline(s) active agents are present in the formulation at a concentration of about 1 to about 25% (w/v). In some embodiments of the invention, the isoxazoline active agents are present in the formulation as a concentration from about 1 to about 20% (w/v), about 1 to about 10% (w/v), about 5 to about 15% (w/v), or about 5 to 10% (w/v). In other embodiments, the isoxazoline active agent(s) are present in the compositions at a concentration of about 1 to about 5% (w/v), about 3-6% (w/v) or about 0.5% to about 2.0% (w/v).

The volume of the topical composition applied is not restricted as long as the amount of substance administered is practical and shown to be safe and effective. Typically, the volume applied depends on the size and weight of the animal as well as the concentration of active, the extent of infestation by parasites and the type of administration. For spot-on compositions, the volume applied is typically of the order of about 0.1 ml to about 10 ml, about 0.1 ml to about 5 ml, or about 0.1 to about 1 ml, or, or. In other embodiments, the volume may be about 4 ml to about 7 ml. For larger animals, the volume may be higher including, but not limited to, up to 10 ml, up to 20 ml or higher. In one embodiment of the volume, the volume is on the order of about 0.5 ml to about 1 ml or about 0.5 ml to about 2 ml for cats, and on the order of about 0.3 to about 3 ml or 4 ml for dogs, depending on the weight of the animal.

For the pour-on form of the composition, the volume applied can be of the order of about 0.3 to about 100 mL. In other embodiments, volume applied of the pour-on formulations may be about 1 ml to about 100 ml or about 1 ml to about 50 ml. In still other embodiments, the volume may be about 5 ml to about 50 ml or about 10 ml to about 100 ml.

Dosage forms may contain from about 0.5 mg to about 5 g of a combination of active agents. More typically, the amount of active is present in an amount of from about 1 mg to about 500 mg of an active agent, about 1 mg to about 100 mg or about 1 mg to about 25 mg. In still other embodiments, the amount of the active agent present in the compositions is about 10 mg about 50 mg or about 10 mg to about 100 mg. In other embodiments, the amount of active agent present in the compositions is about 50 mg to about 200 mg, about 100 mg to about 300 mg, about 100 mg to about 400 mg, about 200 mg to about 500 mg, about 300 mg to about 600 mg, about 400 mg to about 800 mg, or about 500 mg to about 1000 mg.

The compositions of the invention are made by mixing the appropriate amount of the active agents, pharmaceutically acceptable carrier or diluent and optionally a crystallization inhibitor, antioxidant, preservative, film former, etc., to form a composition of the invention. In some embodiments the composition can be obtained by following the method of making these forms described above by the description of making these forms found in general formulation text known to those in the art, e.g. *Remington—The Science and Practice of Pharmacy* (21$^{st}$ Edition) (2005), *Goodman & Gilman's The Pharmacological Basis of Therapeutics* (11$^{th}$ Edition) (2005) *and Ansel's Pharmaceutical Dosage Forms and Drug Delivery Systems* (8$^{th}$ Edition), edited by Allen et al., Lippincott Williams & Wilkins, (2005).

Methods of Treatment

In another aspect of the invention, a method for preventing or treating a parasite infestation/infection in an animal is provided, comprising administering to the animal a topical composition comprising an effective amount of at least one isoxazoline active agent together with a pharmaceutically acceptable carrier that is suitable for application to the skin of the animal. The compositions or formulations of the invention have long-lasting efficacy against ectoparasites (e.g. fleas and ticks) and in certain embodiments may also active against endoparasites that harm animals.

In one embodiment of the invention, methods for the treatment or prevention of a parasitic infestation or infection in a domestic animal are provided, which comprise administering a topical composition comprising an effective amount of at least one isoxazoline active agent to the animal. Ectoparasites against which the methods and compositions of the invention are effective include, but are not limited to, fleas, ticks, mites, mosquitoes, flies and lice. In certain embodiments wherein the compositions include one or more additional active agents that are active against internal parasites the compositions and methods of the invention may also effective against endoparasites including, but not limited to, cestodes, nematodes, hookworms and roundworms of the digestive tract of animals and humans.

In one embodiment for treatment against ectoparasites, the ectoparasite is one or more insect or arachnid including those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp. including *Haematobia irritans, Musca* sp., *Stomoxys* sp. including *Stomoxys calcitrans, Dematobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vituli,* etc.; and mites such as *Sarcoptes scabiei* and *Psoroptes ovis*. The above list is not exhaustive and other ectoparasites are well known in the art to be harmful to animals and humans. These include, for example migrating dipterous larvae.

In some embodiments of the invention, the composition can also be used to treat against endoparasites such as those helminths selected from the group consisting of *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris,* and *Trichostrongylus,* among others.

In one embodiment, the invention provides methods for the treatment and prevention of parasitic infections and infestations of animals (either wild or domesticated), including livestock and companion animals such as cats, dogs, horses, birds including chickens, sheep, goats, pigs, turkeys and cattle, with the aim of ridding these hosts of parasites commonly encountered by such animals.

In a preferred embodiment, the invention provides methods and compositions for the treatment or prevention of parasitic infections and infestations in companion animals including, but not limited to, cats and dogs. The methods and compositions are particularly effective for preventing or treating parasitic infestations of cats and dogs with fleas and ticks.

In another preferred embodiment, the methods and compositions of the invention are used for the treatment or prevention of parasitic infections and infestations in cattle or sheep. When treating livestock animals such as cattle or sheep, the methods and compositions are particularly effective against *Rhipicephalus* (*Boophilus*) *microplus, Haematobia irritans* (horn fly), *Stomoxys calcitrans* (stable fly), and sheep myiases such as *Lucilia sericata, Lucilia cuprina* (known as blowfly strike in Australia, New Zealand and South Africa).

The terms "treating" or "treat" or "treatment" are intended to mean the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

The compositions of the invention are administered in parasiticidally effective amounts which are which are suitable to control the parasite in question to the desired extent, as described below. In each aspect of the invention, the compounds and compositions of the invention can be applied against a single pest or combinations thereof.

The compositions of the invention may be administered continuously, for treatment or prevention of parasitic infections or infestations. In this manner, the compositions of the invention deliver an effective amount of the active compounds to the animal in need thereof to control the target parasites. By "effective amount" is intended a sufficient amount of a composition of the invention to eradicate or reduce the number of parasites infesting the animal. In some embodiments, an effective amount of the active agent achieves at least 70% efficacy against the target parasite. In other embodiments, an effective amount of the active agent achieves at least 80%, or at least 90% efficacy against the target pests. Preferably, an effective amount of the active agent will achieve at least 95%, at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In some embodiments for companion animals, the dose of the isoxazoline active agent administered from the topical compositions of the invention is between about 0.1 to about 30 mg per kg of body weight. More typically the dose of the isoxazoline active agent administered is about 0.5 to about 20 mg/kg or about 0.5 to about 15 mg/kg body weight. Preferably, the dose of the isoxazoline active agent administered is about 0.5 to about 10 mg/kg, about 0.5 to about 8 mg/kg or about 0.5 to about 5 mg/kg of body weight.

In certain embodiments for the treatment and prevention of parasite infestations and infections in cats, the dose of the isoxazoline active agent administered will be about 0.5 to about 2 mg/kg of body weight, preferably about 1 mg/kg of bodyweight. In other embodiments for the very long lasting treatment and protection of cats against parasitic infestations or infections a dose of about 2 to about 15 mg/kg of bodyweight or preferably about 5 to about 15 mg/kg of bodyweight will be administered.

In some embodiments for the treatment and protection of dogs from parasitic infestations and infections, a dose of about 2 to about 15 mg/kg of bodyweight of the isoxazoline active agent will be administered. In other embodiments, a dose of about 2 to about 8 mg/kg or about 2 to about 5 mg/kg of bodyweight will be administered.

In other embodiments for the treatment of livestock animals such as cattle or sheep, doses of the isoxazoline active agent administered may be about 1 to about 30 mg/kg of body weight. More typically the doses administered will be about 1 to about 20 mg/kg or about 1 to about 15 mg/kg. Preferably, a dose of the isoxazoline active agent administered to livestock animals will be about 1 to about 10 mg/kg of body weight.

Higher amounts may be provided for very prolonged release in or on the body of the animal. In another treatment embodiment, the amount of active agents for birds and other animals which are small in size is greater than about 0.01 mg/kg, and in another embodiment for the treatment of small-sized birds and other animals, the amount of is between about 0.01 and about 20 mg/kg of weight of animal. More typically the dose of the isoxazoline for small-sized animals and birds is about 0.5 to about 15 mg/kg, about 0.5 to about 10 mg/kg of body weight, or about 0.5 mg/kg to about 5 mg/kg of body weight.

In one embodiment of the method of use in dogs or cats, a composition comprising an isoxazoline compound has an efficacy against fleas and/or ticks of at least about 90.0% or higher for about 1 month, or longer. In another embodiment, the compositions of the invention provide an efficacy against fleas and/or ticks of at least 95.0% or higher for about 30 days, or longer.

In another embodiment, the topical compositions of the invention provide an efficacy against fleas and/or ticks in cats and dogs of at least about 80% for two months, or longer. In another embodiment, the topical compositions provide efficacy against fleas and/or ticks in cats and dogs of about 90% for about two months, or longer. In still another embodiment, the compositions provide an efficacy of about 95% for about 2 months or longer.

In another embodiment, the composition has an efficacy of at least about 80% against fleas and/or ticks for about 3 months, or longer. In still another embodiment, the topical compositions of the invention provide an efficacy of at least about 90% against fleas and/or ticks for 3 months or longer. In yet another embodiment, the topical compositions of the invention provide an efficacy of at least about 95% against fleas and/or ticks for 3 months or longer. In still another embodiment, the topical compositions of the invention provide an efficacy against fleas and/or ticks in cats and/or dogs of at least 80% or at least 90% for about 3 months to about 6 months or longer.

In one embodiment of the invention, the topical spot-on compositions of the invention are administered to the animal over a localized region of the animal, e.g. between the two shoulders. In one embodiment of the invention, the localized region has a surface area of about 10 cm$^2$ or larger. In another embodiment of the invention, the localized region has a surface area of between about 5 and about 10 cm$^2$, or smaller.

In another embodiment of the invention, the pour-on topical compositions of the invention will be administered in a line along the back of the animal approximately between the shoulders and the hind quarters.

The solutions according to the invention may be applied using any means known per se, e.g. using an applicator gun or a metering flask, pipette, syringes, roll on, droppers, capsules, foil packages, vials, twist tip containers, metered-dose aerosols or sprays and other single dose and multi-dose containers.

In another aspect of the invention, a kit for the treatment or prevention of a parasitic infestation in an animal is provided, which comprises at least one isoxazoline active agent together with a pharmaceutically acceptable carrier and a dispensing device for topical application of the composition. The dispensing device may be a pipette, syringes, roll on, droppers, capsules, foil packages, vials, twist tip containers, metered-dose aerosols or sprays and other single dose and multi-dose containers, which includes an effective dose of each active agent in the pharmaceutically acceptable carrier or diluent.

An important aspect of the invention is to provide a multiple-use container comprising a topical composition of the invention, from which accurate single dose aliquots of the long lasting topical formulations may be administered. The formulation must remain stable with repetitive exposure to the outside environment, particularly oxygen and water. This embodiment may be particularly useful with the very long lasting formulations of the invention that require administration to an animal infrequently, such as once every 3-6 months, or similar. Some solvents such as ethers (including DMI, Transcutol® and the like) give rise to peroxides, which then yield ketones and aldehydes that may be further degraded to acids. The presence of acids may contribute to the degradation of acid hydrolysis-susceptible molecules, including isoxazoline active agents. Thus, formulation stability is particularly important for the multi-dose container application, where the formulations can be exposed to oxygen and water during multiple rounds of opening and closing. Importantly, it was found that the use of certain antioxidants described herein, including BHT and BHA, efficiently inhibit the degradation of the active agent in ether solvents. For example, a 12% (w/v) solution of Compound A in DMI exhibited no significant change in assay over the course of an eleven week accelerated stability study at 50° C. in clear glass containers. In other embodiments, antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol and the like, may be added to the topical compositions to inhibit the formation of oxidative species. The antioxidants are generally added to the formulation in amounts of from about 0.01 to about 2.0%, based upon total weight of the formulation, with about 0.05 to about 1.0% being especially preferred.

EXAMPLES

The invention is further described by the following non-limiting examples which further illustrate the invention, and are not intended, nor should they be interpreted to, limit the scope of the invention.

Formulation Examples

Liquid vehicles suitable for topical isoxazoline-containing formulations for control of parasites were investigated. As a non-limiting example, the isoxazoline compound 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Cmpd. A), was investigated for topical delivery to animals, including cats, dogs and livestock animals such as cattle. Formulations comprising an isoxazoline compound in combination with one or more additional active agents, including (S)-methoprene, pyriproxyfen and nitenpyram, were also prepared and tested.

Formulations were prepared with a variety of liquid carrier vehicles and evaluated for effectiveness to control ectoparasites, particularly fleas and ticks in cats and dogs, and ticks, mites and lice in cattle. Solvent systems comprising either one solvent, including a diester of a dicarboxylic acid and/or an ether such as dimethyl isosorbide, or a combination of solvents including a diester of a dicarboxylic acid, specifically diethyl sebacate, and at least a second solvent(s) are encompassed by the invention. In various embodiments, formulations comprising a single solvent such as DES or DMI or a combination of solvents were investigated. Solvents combined with a diester of a dicarboxylic acid include, but are not limited to: 1) a propylene glycol ester or ether, including PG monocaprylate, PG caprylate, PG monolaurate, PG dicaprylate/dicaprate, PG caprylic/capric triglycerides (LABRASOL®) or a combination thereof; 2) an ether (e.g. dimethyl isosorbide); 3) a second ester (triacetin, lauryl lactate); 4) a fatty acid ester including, but not limited to, isopropyl palmitate, isostearyl lactate, dibutyl adipate, dibutyl sebacate, octyl palmitate, polyethyleneglycol stearate and cetearyl octanoate; 5) a glycol or polyglycol ether such as Transcutol®, PEG 400 and the like; 6) an oil such as mineral oil, diglycerides, triglycerides, jojoba oil, lecithin and castor oil; 7) a long chain aliphatic alcohol such as isostearyl alcohol; and 8) mixed esters sucrose and carboxylic acids, including sucrose acetate isobutyrate (SAIB) and the like.

In other embodiments, the topical compositions of the invention comprise Transcutol®, glycerol formal, triacetin, propylene carbonate, benzyl alcohol or DMI.

Non-limiting formulations comprising an isoxazoline compound (Cmpd. A) alone or in combination with the non-limiting additional active agents (S)-methoprene, pyriproxyfen and nitenpyram are provided in below.

Formulation 1—Add diethyleneglycol monoethyl ether (Transcutol®) (50% of volume required); Polysorbate 80 and Ethanol are added; the BHA, BHT, povidone 17, and Cmpd. A are then added and mixed until dissolved, and the mixture is QS with Transcutol®.

| Ingredients | Function | % |
| --- | --- | --- |
| Cmpd. A | Active | 3.7, 6.0 w/v |
| (S)-methoprene | Active | 9.0 w/v |
| Polysorbate 80 | Surfactant | 5.0 w/v |
| Ethanol | Spreading agent | 10.0 v/v |
| Butylated hydroxyanisole | Antioxidant | 0.02 w/v |
| Butylated hydroxy toluene | Antioxidant | 0.01 w/v |
| Povidone K-17 | Thickener | 5.0 w/v |
| Diethylene glycol monoethyl ether | Solvent | QS |

Formulation 2—Add glycerol formal (GF, 50% of required volume), add Cmpd. A, dissolve; add DMI; add (s)-methoprene; QS GF.

| Ingredients | Function | % |
| --- | --- | --- |
| Cmpd. A | Active | 3.7, 6.0 w/v |
| (S)-methoprene | Active | 9.0 w/v |
| Dimethyl isosorbide | Permeation enhancer | 25 w/v |
| Glycerol formal (GF) | Spreading agent | QS |

Formulation 3—Add diisopropyl adipate (DIPA, 50% of required volume), add Cmpd. A, dissolve; add (s)-methoprene; QS DIPA

| Ingredients | Function | % |
| --- | --- | --- |
| Cmpd. A | Active | 3.7, 6.0 w/v |
| (S)-methoprene | Active | 9.0 w/v |
| Diisopropyl adipate (DIPA) | Spreading agent | QS |

Formulation 4—Add diethyl sebacate (DES 50% of required volume); add PG monolaurate; add Cmpd. A, dissolve; add (S)-methoprene; QS DES.

| Ingredients | Function | % |
| --- | --- | --- |
| Cmpd. A | Active | 6.0 w/v |
| (S)-methoprene | Active | 9.0 w/v |
| Propylene glycol monolaurate | Permeation enhancer | 25.0 v/v |
| DES | Spreading agent | QS |

Formulation 5—Add DES (50% of required volume); add PG monocaprylate; add Cmpd. A, dissolve; add (S)-methoprene; QS DES.

| Ingredients | Function | % |
| --- | --- | --- |
| Cmpd. A | Active | 6.0 w/v |
| (S)-methoprene | Active | 9.0 w/v |
| Propylene glycol monocaprylate (Capryol 90) | Permeation enhancer | 25.0 v/v |
| DES | Spreading agent | QS |

Formulation 6—Add DIPA (50% of required volume); add Ethyl hexyl pelargonate; add Cmpd. A, dissolve; add (S)-methoprene; QS DIPA

| Ingredients | Function | % |
| --- | --- | --- |
| Cmpd. A | Active | 6.0 w/v |
| (S)-methoprene | Active | 9.0 w/v |
| Ethyl hexyl pelargonate | Permeation enhancer | 25.0 v/v |
| DIPA | Spreading agent | QS |

Formulation 7—Add DIPA (50% of required volume); add diisopropyl sebacate; add silicone fluid; add Cmpd. A, dissolve; add (S)-methoprene; QS DIPA

| Ingredients | Function | % |
| --- | --- | --- |
| Cmpd. A | Active | 6.0 w/v |
| (S)-methoprene | Active | 9.0 w/v |
| Diisopropyl sebacate | Permeation enhancer | 25.0 v/v |
| Silicone fluid | Spreading agent | 3 v/v |
| DIPA | Spreading agent | QS |

Formulation 8—Add Miglyol 840 (50% of required volume); add lauryl lactate; add Cmpd. A, dissolve; add (S)-methoprene; QS Miglyol 840

| Ingredients | Function | % |
| --- | --- | --- |
| Cmpd. A | Active | 6.0 w/v |
| (S)-methoprene | Active | 9.0 w/v |
| Lauryl lactate | Permeation enhancer | 25.0 v/v |
| Miglyol 840 | Spreading agent/ permeation enhancer | QS |

Formulation 9—Add Miglyol 840 (50% of required volume); add triacetin; add Cmpd. A, dissolve; add (S)-methoprene; QS Miglyol 840

| Ingredients | Function | % |
| --- | --- | --- |
| Cmpd. A | Active | 6.0 w/v |
| (S)-methoprene | Active | 9.0 w/v |
| Triacetin | Permeation enhancer | 25.0 v/v |
| Miglyol 840 | Spreading agent/ permeation enhancer | QS |

Formulation 10—Add Miglyol 840 (50% of required volume); add Cmpd. A, dissolve; add (S)-methoprene; QS Miglyol 840

| Ingredients | Function | % |
| --- | --- | --- |
| Cmpd. A | Active | 6.0 w/v |
| (S)-methoprene | Active | 9.0 w/v |
| Miglyol 840 | Spreading agent/ permeation enhancer | QS |

Formulation 11—Add DES (50% of required volume); add Cmpd. A, dissolve; add (S)-methoprene; QS DES

| Ingredients | Function | % |
| --- | --- | --- |
| Cmpd. A | Active | 3.0, 4.5, 6.0 w/v |
| (S)-methoprene | Active | 9.0 w/v |
| DES | Spreading agent/ permeation enhancer | QS |

Formulation 12—Add DES (50% of required volume); add Cmpd. A, dissolve; QS DES

| Ingredients | Function | % |
| --- | --- | --- |
| Cmpd. A | Active | 6.0 w/v |
| DES | Spreading agent/ permeation enhancer | QS |

Formulation 13—Add DES (50% of required volume); add PG monocaprylate; add Cmpd. A, dissolve; QS DES.

| Ingredients | Function | % |
| --- | --- | --- |
| Cmpd. A | Active | 6.0 w/v |
| Propylene glycol monocaprylate (Capryol 90) | Permeation enhancer | 30.0 v/v |
| DES | Spreading agent | QS |

Formulation 14—Add DES (30% of required volume); add PG dicaprylate/dicaprate and PG monocaprylate; add Cmpd. A, dissolve; add (S)-methoprene QS DES.

| Ingredients | Function | % |
|---|---|---|
| Cmpd. A | Active | 12.0 w/v |
| (S)-methoprene | Active | 9.0% w/v |
| Propylene glycol dicaprylate/dicaprate (Capryol PGMC) | Permeation enhancer | 25.0 v/v |
| Propylene glycol monocaprylate (Capryol 90) | Permeation enhancer | 25.0 v/v |
| DES | Spreading agent | QS |

Formulation 15—Add DES (50% of required volume); add, with stirring, lauryl lactate; add Cmpd. A, dissolve; QS DES

| Ingredients | Function | % |
|---|---|---|
| Cmpd. A | Active | 6.0 w/v |
| Lauryl Lactate | Permeation enhancer | 25.0 v/v |
| DES | Spreading agent | QS |

Formulation 16—Add DIPA (50% of required volume); add DMI; add Cmpd. A, dissolve; QS DIPA

| Ingredients | Function | % |
|---|---|---|
| Cmpd. A | Active | 6.0 w/v w/v |
| Dimethyl isosorbide | Permeation enhancer | 25 v/v |
| Diisopropyl adipate | Spreading agent | QS 100% |

Formulation 17—Add DES (50% of required volume); add DMI; add Cmpd. A, dissolve; QS DES

| Ingredients | Function | % |
|---|---|---|
| Cmpd. A | Active | 12.0 w/v w/v |
| Dimethyl isosorbide (DMI) | Permeation enhancer | 25 v/v |
| DES | Spreading agent | QS 100% |

Formulation 18—Add DES (40% of required volume); add DMI; add Cmpd. A, dissolve; QS DES

| Ingredients | Function | % |
|---|---|---|
| Cmpd. A | Active | 12.0 w/v w/v |
| DES | Spreading agent | 40% w/v |
| Dimethyl isosorbide (DMI) | Permeation enhancer | QS 100% v/v |

Formulation 19—Add DIPA (50% of required volume); add triacetin; add Cmpd. A, dissolve; QS DIPA

| Ingredients | Function | % |
|---|---|---|
| Cmpd. A | Active | 6.0 w/v |
| Triacetin | Permeation enhancer | 25 v/v |
| Diisopropyl adipate | Spreading agent | QS 100% |

Formulation 20—Add DES (60% of required volume); add mineral oil, medium; add Cmpd. A, dissolve; QS DES

| Ingredients | Function | % |
|---|---|---|
| Cmpd. A | Active | 6.0 w/v |
| mineral oil, medium | Substantivity Agent | 25 v/v |
| DES | Spreading agent | QS 100% |

Formulation 21—Add DES (60% of required volume); add mineral oil, light; add Cmpd. A, dissolve; QS DES

| Ingredients | Function | % |
|---|---|---|
| Cmpd. A | Active | 6.0 w/v |
| mineral oil, light | Substantivity Agent | 25 v/v |
| DES | Spreading agent | QS 100% |

Formulation 22—Add DES (60% of required volume); add, with stirring, Transcutol®; add Cmpd. A, mix until dissolved; add SAIB; QS with DES

| Ingredients | Function | % |
|---|---|---|
| Cmpd. A | Active | 6.0 w/v |
| Transcutol ® | Solvent | 20 w/v |
| Sucrose acetate isobutyrate (SAIB) | Controlled release agent | 5 w/v |
| DES | Spreading agent | QS 100% |

Formulation 23—Add DES (60% of required volume); add, with stirring, Transcutol®; add, with stirring, PEG 400; add Cmpd. A, mix until dissolved; QS with DES

| Ingredients | Function | % |
|---|---|---|
| Cmpd. A | Active | 6.0 w/v |
| Transcutol ® | Solvent | 20 w/v |
| PEG 400 | Controlled release agent | 10 w/v |
| DES | Spreading agent | QS 100% |

Formulation 24—Add Transcutol® (60% of required volume); add, with stirring, PEG 400; add Cmpd. A, mix until dissolved; QS Transcutol®

| Ingredients | Function | % |
|---|---|---|
| Cmpd. A | Active | 6.0 w/v |
| PEG 400 | Controlled release agent | 5 w/v |
| Transcutol ® | Solvent & Spreading agent | QS |

Formulation 25—Add DES (60% of required volume); add, with stirring, Transcutol®; add, with stirring, PEG 400; add Cmpd. A, mix until dissolved; QS with DES

| Ingredients | Function | % |
|---|---|---|
| ML Cmpd. A | Active | 6.0 w/v |
| Transcutol ® | Solvent | 20 w/v |
| PEG 400 | Controlled release agent | 10 w/v |
| DES | Spreading agent | QS |

Formulation 26—Add DES (60% of required volume); add, with stirring, PEG 400; add Cmpd. A, mix until dissolved; QS with DES

| Ingredients | Function | % |
|---|---|---|
| Cmpd. A | Active | 6.0 w/v |
| PEG 400 | Solvent and Controlled release agent | 20 w/v |
| DES | Spreading agent | QS |

Formulation 27—Add GF (50% of required volume), add Cmpd. A, dissolve; add nitenpyram, dissolve; add DMI; QS GF.

| Ingredients | Function | % |
| --- | --- | --- |
| Cmpd. A | Active | 0.8 w/v |
| Nitenpyram | Active | 1.0 w/v |
| Dimethyl isosorbide | Permeation enhancer | 25 w/v |
| Glycerol formal | Spreading agent | QS |

Formulation 28—Add DMI (50% of required volume), add Cmpd. A, dissolve; add nitenpyram, dissolve; add (S)-methoprene and dissolve; QS with DMI.

| Ingredients | Function | % |
| --- | --- | --- |
| Cmpd. A | Active | 0.5-2 w/v |
| Nitenpyram | Active | 2-8 w/v |
| (S)-methoprene | Active | 7-10 w/v |
| Dimethyl isosorbide | Solvent | QS |

Formulation 29—Add DMI (50% of required volume), add Cmpd. A, dissolve; add nitenpyram, dissolve; add pyriproxyfen and dissolve; QS DMI.

| Ingredients | Function | % |
| --- | --- | --- |
| Cmpd. A | Active | 0.5-2 w/v |
| Nitenpyram | Active | 2-8 w/v |
| pyriproxyfen | Active | 3-6 w/v |
| Dimethyl isosorbide | Solvent | QS |

Formulation 30—Add Transcutol® (50% of required volume), add Cmpd. A, dissolve; add nitenpyram, dissolve; add pyriproxyfen and dissolve; QS Transcutol®.

| Ingredients | Function | % |
| --- | --- | --- |
| Cmpd. A | Active | 0.5-2 w/v |
| Nitenpyram | Active | 2-8 w/v |
| pyriproxyfen | Active | 3-6 w/v |
| Transcutol ® | Solvent | QS |

Formulation 31—Add GF (50% of required volume), add Cmpd. A, dissolve; add nitenpyram, dissolve; add pyriproxyfen and dissolve; QS GF.

| Ingredients | Function | % |
| --- | --- | --- |
| Cmpd. A | Active | 0.5-2 w/v |
| Nitenpyram | Active | 2-8 w/v |
| pyriproxyfen | Active | 3-6 w/v |
| Glycerol formal | Solvent | QS |

Formulation 32—Add triacetin (50% of required volume), add Cmpd. A, dissolve; add nitenpyram, dissolve; add pyriproxyfen and dissolve; QS triacetin.

| Ingredients | Function | % |
| --- | --- | --- |
| Cmpd. A | Active | 0.5-2 w/v |
| Nitenpyram | Active | 2-8 w/v |
| pyriproxyfen | Active | 3-6 w/v |
| triacetin | Solvent | QS |

Formulation 33—Add propylene carbonate (50% of required volume), add Cmpd. A, dissolve; add nitenpyram, dissolve; add pyriproxyfen and dissolve; QS propylene carbonate.

| Ingredients | Function | % |
| --- | --- | --- |
| Cmpd. A | Active | 0.5-2 w/v |
| Nitenpyram | Active | 2-8 w/v |
| pyriproxyfen | Active | 3-6 w/v |
| Propylene carbonate | Solvent | QS |

Cmpd. A was found to be stable in at least DES, DIPA, DMI, triacetin, GF and propylene carbonate (at 50° C. in glass bottles).

BIOLOGICAL EFFICACY EXAMPLES

Example 1: Efficacy of a Spot-on Composition Comprising a Combination of Cmpd. A and (S)-Methoprene Against *Dermacentor variabilis* Ticks and *Ctenocephalides felis* Fleas in Dogs Twenty eight beagle dogs were studied to determine the effectiveness of a combination of Cmpd. A and (S)-methoprene when administered once as a topical solution against induced infestations of *Dermacentor variabilis* and *Ctenocephalides felis*.

Four Treatment Groups containing seven dogs each were formed. Dogs in Group 1 were untreated (control). Dogs in Groups 2, 3 and 4 were treated topically with spot-on compositions comprising 3.7% (w/v) Cmpd. A and 9% (w/v) (S)-methoprene administered to deliver 2.5 mg/kg Cmpd. A and 6 mg/kg (S)-methoprene (Group 2: Transcutol with 10% (w/v) ethanol, 5% (w/v) TWEEN 80 and 5% (w/v) polyvinylpyrrolidone; Group 3: DMI and glycerol formal (GF); and Group 4: DIPA). All dogs were treated once on Day 0.

All dogs were infested with approximately 100 *C. felis* on Days −1, 8, 15, 22, 29, 35, 43 and 57, and for all Groups except 5, on Day 71. All dogs were also infested with approximately 50 *D. variabilis* on Days −1, 7, 14, 21, 28, 34 and 42. Fleas were counted upon removal on Day −6. Both ticks and fleas were counted upon removal on Days 2, 9, 16, 23, 30, 36 and 44. Fleas only were counted upon removal for all Treatment Groups on Day 58 and for all Treatment Groups except 5 on Day 72. Flea efficacy is listed in Table 1 and tick efficacy is listed in Table 2 below.

Blood samples were collected from all dogs in the study on Days −6, 0 (at 4 h and 12 h), 1, 2, 9, 16, 23, 30, 36, 44, 51, 58, 64, 72, 79 and 86. Plasma samples were analyzed for the concentration of Compound A using an LC/MS/MS analytical method that was GLP validated for the purpose.

Percent reduction (also referred as efficacy) against fleas was 100% through and including Day 30 for all treatment groups (see Table 1). Percent reduction against fleas was above 95% through Day 58 for Group 3.

The percent reduction against ticks was >94% through and including Day 23 (48 hours infestation, see Table 2). Percent reduction was >92% for Groups 6 and 7 on Day 30.

These study data demonstrate that topical formulations comprising Cmpd. A and (S)-methoprene in three different carrier vehicles provided 100% percent reduction for fleas through Day 30 for all treated groups. Tick efficacy was 100% on Days 9 and 16 and two treatment groups (6 and 7) were ≥92% on Day 30.

TABLE 1

Efficacy of a Spot-on Composition Comprising a Combination of Cmpd. A and (S)-methoprene *Ctenocephalides felis*

| | % Reduction Fleas | | | | | | | | |
|---|---|---|---|---|---|---|---|---|---|
| Treatment Group | Day 2 | Day 9 | Day 16 | Day 23 | Day 30 | Day 36 | Day 44 | Day 58 | Day 72 |
| Group 2 % Reduction | 100.0 | 100.0 | 100.0 | 100.0 | 100.0 | 100.0 | 86.5 | 33.2 | — |
| Group 3 % Reduction | 100.0 | 100.0 | 100.0 | 100.0 | 100.0 | 100.0 | 99.6 | 98.5 | 89.0 |
| Group 4 % Reduction | 100.0 | 100.0 | 100.0 | 100.0 | 100.0 | 99.8 | 95.2 | 89.3 | 68.9 |

TABLE 2

Efficacy of a Spot-on Composition Comprising a Combination of Cmpd. A and (S)-methoprene Against *Dermacentor variabilis* Ticks

| | % Reduction Ticks | | | | | | |
|---|---|---|---|---|---|---|---|
| Treatment Group | Day 2 | Day 9 | Day 16 | Day 23 | Day 30 | Day 36 | Day 44 |
| Group 2 % Reduction | 89.0 | 100.0 | 100.0 | 94.8 | 65.0 | 23.3 | 20.7 |
| Group 3 % Reduction | 88.5 | 100.0 | 100.0 | 99.2 | 94.6 | 88.3 | 77.6 |
| Group 4 % Reduction | 84.3 | 100.0 | 100.0 | 97.2 | 92.0 | 52.2 | 57.0 |

Example 2: Efficacy of Spot-on Formulations Containing Compound A and (S)-Methoprene Against *Ctenocephalides felis*

Following the initial studies described in Example 1, additional topical formulations comprising Compound A in combination with an insect growth regulator, (S)-methoprene, in carrier vehicles comprising both a spreading solvent and a permeation solvent were studied. Thus, the efficacy of five different topical formulations comprising Compound A and (S)-methoprene against the cat flea (*Ctenocephalides felis*) in dogs was determined using to a protocol similar to that of Example 1.

Seven Treatment Groups with four dogs each were evaluated. Dogs in Group 1 were untreated, and served as a control group. Dogs in Groups 2-6 were treated topically with formulations comprising Cmpd. A and (S)-methoprene in different carrier vehicles administered at 4.0 mg/kg Cmpd. A+(S)-methoprene administered at 6 mg/kg (Group 2: Miglyol 840; Group 3: DIPA/25% triacetin; Group 4: DIPA/25% DMI; Group 5 DIPA/25% ethyl hexyl pelargonate; and Group 6: DIPA+25% diisopropyl sebacate+3% silicone fluid). Dogs in Group 7 were treated at a dose level of 7.0 mg/kg Compound A+(S)-methoprene at 6 mg/kg with a formulation comprising DIPA+25% diisopropyl sebacate+3% silicone fluid. The concentrations of Compound A and (S)-methoprene in formulations of Groups 2-5 were 6.0% (w/v) and 9.0% (w/v), respectively, and the concentration of Compound A and (S)-methoprene in formulations of Groups 6 and 7 were 10.5% (w/v) and 9% (w/v), respectively.

Dogs were infested with approximately 100 *C. felis* fleas on Day −1. Dogs were treated with the respective topical formulations on Day 0. Fleas were removed and counted on Day 2. Infestations with about 100 fleas were also made on Days 8, 15, 22, 29, 36 and 43. Fleas were combed and counted 24±3 hours after infestation on Days 9, 16, 23, 30, 37 and 44.

Table 3 below provides the % efficacy for each of the topical formulations. As demonstrated by the data, each of the formulations was highly efficacious against the cat flea through at least 44 days.

TABLE 3

Efficacy of Spot-on Composition Against *Ctenocephalides felis*

| | Geometric Mean Flea Count/% Reduction | | | | | | |
|---|---|---|---|---|---|---|---|
| Treatment Group | Day 2 | Day 9 | Day 16 | Day 23 | Day 30 | Day 37 | Day 44 |
| Group 2 % Reduction | 100.0 | 100.0 | 100.0 | 100.0 | 100.0 | 100.0 | 98.6 |
| Group 3 % Reduction | 100.0 | 99.6 | 100.0 | 100.0 | 100.0 | 100.0 | 100.0 |
| Group 4 % Reduction | 100.0 | 100.0 | 100.0 | 100.0 | 100.0 | 100.0 | 100.0 |
| Group 5 % Reduction | 100.0 | 100.0 | 100.0 | 100.0 | 100.0 | 100.0 | 100.0 |
| Group 6 % Reduction | 99.6 | 100.0 | 100.0 | 100.0 | 100.0 | 100.0 | 100.0 |
| Group 7 % Reduction | 100.0 | 100.0 | 100.0 | 100.0 | 100.0 | 100.0 | 100.0 |

Example 3: Efficacy of Spot-on Formulations Containing Compound A and (S)-Methoprene Against *Rhipicephalus Sanguineus*

In another study, the efficacy against ticks of additional topical formulations comprising isoxazoline Compound A in combination with (S)-methoprene in further carrier vehicles comprising both a spreading solvent and a permeation-enhancing solvent was determined. Thus, six topical formulations comprising Compound A and (S)-methoprene were tested for efficacy against *Rhipicephalus Sanguineus* ticks in beagle dogs according to a protocol similar to that of Example 1.

Seven Treatment Groups with four dogs each were evaluated. Dogs in Group 1 were untreated, and served as a control group. Dogs in Groups 2-6 were treated topically with Cmpd. A in different carrier vehicles administered at 4.0 mg/kg+(S)-methoprene administered at 6 mg/kg (Group 2: Miglyol 840/25% lauryl lactate; Group 3: DIPA/25% triacetin; Group 4: DIPA/25% DMI; Group 5 DIPA/25% Capryol 90/25% Capryol PGMC; and Group 6: DES/25% propylene glycol monolaurate). Dogs in Group 7 were treated at a dose level of 7.0 mg/kg Compound A+(S)-methoprene at 6 mg/kg with a formulation comprising DES/25% propylene glycol monolaurate. The concentrations of Compound A and (S)-methoprene in the formulations used with Groups 2-6 were 6.0% (w/v) and 9.0% (w/v), respectively. The concentrations of Compound A and (S)-methoprene in the formulation used with Group 7 were 10.5% (w/v) and 9% (w/v), respectively.

All dogs were infested with approximately 50 *R. sanguineus* on Days −1, 7, 14, 21, 28, 35, 42, 49, 56 and 63. Further, Treatment Groups 1, 5, 6 and 7 only were infested on Days 70, 77 and 84, and Treatment Groups 1, 6 and 7 only on Day 91. Ticks were counted upon removal on Days 2, 9, 16, 23, 30, 37, 44, 51, 58 and 65. Tick counts were conducted for Treatment Groups 1, 5, 6 and 7 only on Days 72, 79 and 86 and Treatment Groups 1, 6 and 7 only on Day 93.

Tables 4A and 4B below presents the efficacy of the spot-on formulations administered to Groups 2-7 against *R. sanguineus*.

TABLE 4A

Efficacy Against *Rhipicephalus Sanguineus* in Dogs

| Treatment Group | % Reduction Ticks | | | | | | |
|---|---|---|---|---|---|---|---|
| | Day 2 | Day 9 | Day 16 | Day 23 | Day 30 | Day 37 | Day 44 |
| Group 2 % Reduction | 96.9 | 100.0 | 100.0 | 100.0 | 100.0 | 100.0 | 98.6 |
| Group 3 % Reduction | 94.5 | 100.0 | 100.0 | 100.0 | 94.5 | 97.9 | 97.7 |
| Group 4 % Reduction | 98.2 | 100.0 | 100.0 | 100.0 | 97.5 | 94.5 | 98.6 |
| Group 5 % Reduction | 98.2 | 100.0 | 100.0 | 98.1 | 100.0 | 97.9 | 100.0 |
| Group 6 % Reduction | 100.0 | 100.0 | 100.0 | 100.0 | 100.0 | 100.0 | 100.0 |
| Group 7 % Reduction | 96.9 | 100.0 | 100.0 | 100.0 | 100.0 | 100.0 | 100.0 |

TABLE 4B

Efficacy Against *Rhipicephalus Sanguineus* in Dogs (continued)

| Treatment Group | % Reduction Ticks | | | | | | |
|---|---|---|---|---|---|---|---|
| | Day 51 | Day 58 | Day 65 | Day 72 | Day 79 | Day 86 | Day 93 |
| Group 2 % Reduction | 100.0 | 91.3 | 80.3 | ND[1] | ND | ND | ND |
| Group 3 % Reduction | 95.5 | 89.9 | 65.2 | ND | ND | ND | ND |
| Group 4 % Reduction | 96.4 | 82.2 | 77.1 | ND | ND | ND | ND |
| Group 5 % Reduction | 96.7 | 94.7 | 87.6 | 89.1 | 86.9 | 67.2 | ND |
| Group 6 % Reduction | 96.7 | 100.0 | 100.0 | 94.7 | 90.1 | 56.0 | 42.1 |
| Group 7 % Reduction | 98.3 | 97.7 | 95.5 | 94.7 | 100.0 | 84.5 | 75.1 |

[1]ND = not done

As Tables 4A and 4B show, Groups 3 and 4 maintained at least a 90% reduction in tick count through Day 51, Groups 2 and 5 through Day 58, and Groups 6 and 7 through Day 79. In particular, Treatment Groups 6 and 7 demonstrated superior efficacy for an extended period of time. Thus, formulations comprising a combination of an isoxazoline and an insect growth regulator in a carrier vehicle comprising a combination of a spreading solvent and a permeation enhancer were determined to provide surprisingly long lasting efficacy against *R. sanguineus*.

Example 4: Dose Characterization of Spot-on Formulations of Cmpd. A Against *Amblyomma americanum* Ticks in Dogs The efficacy of a spot-on composition of the invention comprising an isoxazoline compound (Cmpd. A) in a carrier vehicle comprising either DES alone or DES+lauryl lactate (LL), against ticks (*Amblyomma americanum*), in dogs was studied. The compositions contained 3.0%, 4.5%, or 6.0% Cmpd. A in either DES alone or DES+lauryl lactate, which delivered doses of 4.0 mg/kg, 3.0 mg/kg, and 2 mg/kg, respectively, of Cmpd. A to dogs infested with *A. Americanum* ticks.

Seven Treatment Groups were evaluated. Treatment Group 1 was administered a placebo formulation and served as a control. Treatment Groups 2, 3 and 4 were administered a topical formulation comprising 6.0% (w/v), 4.5% (w/v) and 3.0% (w/v) of Cmpd. A in DES, respectively, corresponding to doses of 4.0 mg/kg, 3.0 mg/kg and 2.0 mg/kg, respectively. Treatment Groups 5, 6 and 7 were administered a topical formulation comprising 6.0% (w/v), 4.5% (w/v) and 3.0% (w/v) of Cmpd. A in DES+9% lauryl lactate, respectively, corresponding to doses of 4.0% mg/kg, 3.0 mg/kg and 2.0 mg/kg body weight Cmpd. A, respectively.

All dogs were treated once topically on Day 0 by parting the hair and applying the solution from a syringe directly onto the skin in a single spot on the midline of the neck between the base of the skull and the shoulder blades.

All dogs were infested with approximately 50 *A. americanum* on Days −1, 7, 14, 21, 28, 35 and 42. Ticks were counted upon removal on Days 2, 9, 16, 23, 30, 37 and 44. The % reduction of ticks for each Group is presented Table 5 below.

Blood samples were collected from all dogs on Days −5, 0 (at 4 h and 12 h), 1, 2, 9, 16, 23, 30, 37 and 44. Plasma samples were analyzed for the concentration of Compound A using a LC/MS/MS method that was GLP validated for the analysis of the compound.

Treatment Groups 5 and 6 (4.0 mg/kg and 3.0 mg/kg Cmpd. A in DES+LL, respectively) maintained at least 90% efficacy through five weeks, and Treatment Group 2 (4.0 mg/kg in DES alone) maintained at least 90% efficacy through Week 3.

TABLE 5

Efficacy Against *Amblyomma americanum* in Dogs

| Treatment Group | % Reduction Ticks | | | | | | |
|---|---|---|---|---|---|---|---|
| | Day 2 | Day 9 | Day 16 | Day 23 | Day 30 | Day 37 | Day 44 |
| Group 2 % Reduction | 97.4 | 100.0 | 100.0 | 100.0 | 82.5 | 97.9 | 84.2 |
| Group 3 % Reduction | 90.0 | 100.0 | 97.6 | 82.0 | 70.0 | 80.4 | 56.0 |
| Group 4 % Reduction | 95.4 | 100.0 | 100.0 | 79.5 | 90.3 | 57.1 | 38.8 |
| Group 5 % Reduction | 100.0 | 100.0 | 100.0 | 94.3 | 100.0 | 89.0 | 84.8 |
| Group 6 % Reduction | 98.4 | 100.0 | 100.0 | 93.1 | 92.1 | 89.0 | 53.6 |
| Group 7 % Reduction | 98.4 | 100.0 | 100.0 | 80.6 | 88.9 | 74.6 | 42.4 |

Example 5: Dose Characterization and Determination of Speed of Kill of a Single Spot-on Treatment with Formulations of Cmpd. A Against *Ctenocephalides felis* Fleas and *Rhipicephalus sanguineus* Ticks on Dogs The efficacy of a formulation comprising an isoxazoline compound (Cmpd. A) in a carrier comprising 40% DES/DMI against *Ctenocephalides felis* fleas and *Rhipicephalus sanguineus* ticks in Dogs was studied. As discussed above, DES is a solvent with good spreading properties and DMI exhibits good permeation properties. Three treatment groups containing three dogs each were evaluated. All dogs were treated once topically on Day 0 by parting the hair and applying the solution from a syringe directly onto the skin in a single spot on the midline of the neck between the base of the skull and the shoulder blades.

Treatment Group 1 was a placebo control and received 0.067 mL/kg of body weight. Treatment Group 2 was administered a topical spot-on formulation comprising 6.0% (w/v) Cmpd. A in 40% DES/DMI to deliver a dose of 4.0 mg/kg body weight. Treatment Group 3 was administered a topical spot-on formulation comprising 12% (w/v) Cmpd. A in 40% DES/DMI to deliver a dose of 4.0 mg/kg body weight.

All dogs were infested with approximately 100 *C. felis* on Days −1, 7, 14, 21, 28, 35 and 42. Fleas were counted upon removal from dogs approximately 24 hours post infestation on Days 1, 8, 15, 22, 29, 36 and 43. The % reduction (efficacy) of each Treatment Group over time is listed in Tables 6A, 6B and 7, respectively.

TABLE 6A

Efficacy Against *Ctenocephalides felis* in Dogs - Day 0 to Day 22

| Treatment Group | Day 1 | Day 8 | Day 15 | Day 22 |
|---|---|---|---|---|
| Group 2 % Reduction | 100.0 | 100.0 | 100.0 | 100.0 |
| Group 3 % Reduction | 100.0 | 100.0 | 100.0 | 100.0 |

TABLE 6B

Efficacy Against *Ctenocephalides felis* in Dogs - Day 28 to Day 43

| Treatment Group | Day 29 | Day 36 | Day 43 |
|---|---|---|---|
| Group 2 % Reduction | 100.0 | 100.0 | 99.2 |
| Group 3 % Reduction | 100.0 | 100.0 | 100.0 |

The percent efficacy against ticks is presented in Table 7. Both Treatment Groups demonstrated good efficacy at least through 31 days.

TABLE 7

Efficacy against *Rhipicephalus sanguineus* Ticks

| Treatment Group | Day 2 | Day 30 | Day 31 | Day 38 |
|---|---|---|---|---|
| Control | | | | |
| Group 2 % Reduction | 100.0 | 91.5 | 100.0 | 85.2 |
| Group 3 % Reduction | 100.0 | 72.6 | 100.0 | 51.3 |

Example 6: Efficacy of Spot-on Formulations Comprising Compound A at Different Doses Against *Rhipicephalus sanguineus* Ticks in Dogs A further study was conducted to examine the efficacy of a topical formulations comprising Compound A in three different formulations containing DES against ticks in dogs. Twenty-four beagles were studied to determine the effectiveness against induced infestations of *Rhipicephalus sanguineus* of spot-on formulations comprising Cmpd. A in different carriers administered at 4.0 mg/kg to dogs.

Treatment Group 1 dogs were treated with a placebo solution. Treatment Group 2 was treated with a formulation comprising 6% (w/v) Cmpd. A in DES; Treatment Group 3 were treated with a composition comprising 6% (w/v) Cmpd. A in 40% DES/DMI; and Treatment Group 4 were treated with a formulation comprising 6% (w/v) Cmpd. A in DES with 30% Capryol 90. All dogs were treated once topically on Day 0. Topical solutions were applied by parting the hair and applying the solution from a syringe directly onto the skin in a single spot on the midline of the neck between the base of the skull and the shoulder blades.

All dogs were infested with approximately 50 *R. sanguineus* on Days −1, 7, 14, 21, 28, 35 and 42. Ticks were counted upon removal from dogs on Days 2, 9, 16, 23, 30, 37, and 44. All ticks were counted upon removal at 48 (±3) hours post treatment or infestation.

The percent efficacies of the treated groups compared to the untreated control group were determined for the 48 hour post-treatment/infestation counts. Percent efficacy for each counting time 48 hours after treatment or infestation are listed in Table 8. Treatment Group 3 maintained ≥90% efficacy 48 hours after infestation at every sampling time from Day 9 through Day 44. Treatment Group 2 was able to maintain at least 90% efficacy 48 hours after infestation throughout the six weeks of the study.

TABLE 8

Efficacy Against *Rhipicephalus sanguineus* in Dogs

| Treatment Group | Day 2 | Day 9 | Day 16 | Day 23 | Day 30 | Day 37 | Day 44 |
|---|---|---|---|---|---|---|---|
| Group 2 % Reduction | 93.2 | 100.0 | 100.0 | 100.0 | 97.8 | 95.3 | 97.5 |
| Group 3 % Reduction | 72.8 | 100.0 | 100.0 | 100.0 | 100.0 | 93.5 | 82.9 |
| Group 4 % Reduction | 97.2 | 100.0 | 100.0 | 100.0 | 98.4 | 96.1 | 78.1 |

Example 7: Efficacy of Spot-on Formulations Comprising Isoxazoline Compound A in Different Carrier Vehicles at 1 mg/kg Against *Ctenocephalides felis* Fleas in Cats The efficacy of several spot-on formulations comprising Cmpd. A dosed at 1 mg/kg body weight in different carrier vehicles against fleas in cats was studied. Five cats each were allocated to 6 Treatment Groups. The six cats per study group were subjected to weekly infestations followed by 24 h flea counts for 5 to 8 weeks, according to the following Group allocations: Group 1—untreated control; Group 2—1.0% (w/v) Cmpd. A in DMI; Group 3—1.0% (w/v) Cmpd. A in diethyl sebacate (DES); Group 4—1.0% (w/v) Cmpd. A in 9% lauryl lactate+DES; Group 5—1% (w/v) Cmpd. A in 8% ethyl oleate+DES; and Group 6—1% (w/v) Cmpd. A in a vehicle comprising Transcutol®+10% (w/v) ethanol+5% polyvinylpyrrolidone+5% TWEEN 80. Cats were infested with approximately 100 *C. felis* on Day −1 and treated on Day 0 with the corresponding spot-on formulation by application of the formulation directly on the skin in the midline of the neck, between the base of the skull and the shoulder blades in a single spot using a 1 mL syringe. Twelve hours after treatment, fleas were removed and counted. The cats were immediately re-infested with approximately 100 fleas. Fleas were removed and counted on Day 1 at approximately 24 hours post-treatment. Cats were also infested with fleas on Days 7, 21, 38, 35, 42 and 49. Fleas were removed and counted approximately 24 hours after infestation on Days 8, 22, 29, 36, 43 and 50. The efficacy for each formulation is presented in Table 9 below.

TABLE 9

Efficacy of Spot-on Formulations Against *Ctenocephalides felis* Fleas in Cats in Different Formulations at a Dose of 1 mg/kg

| Treatment Group | % Reduction | | | | | | | |
|---|---|---|---|---|---|---|---|---|
| | Day 0 (12 hr) | Day 1 | Day 8 | Day 22 | Day 29 | Day 36 | Day 43 | Day 50 |
| Group 2 % Reduction | 22.3 | 28.0 | 99.3 | 99.5 | 98.5 | 94.2 | 94.3 | 87.7 |
| Group 3 % Reduction | 9.6 | 72.7 | 99.7 | 97.4 | 95.1 | 79.3 | 72.2 | 44.8 |
| Group 4 % Reduction | 9.2 | 36.5 | 99.7 | 98.5 | 98.1 | 89.3 | 92.7 | 79.2 |
| Group 5 % Reduction | 65.9 | 77.2 | 98.4 | 96.9 | 95.0 | 85.5 | 79.7 | 64.0 |
| Group 6 % Reduction | 17.7 | 75.6 | 100.0 | 99.3 | 97.5 | 93.8 | 93.9 | 79.6 |

As Table 9 demonstrates, all of the spot-on formulations comprising Cmpd. A were highly effective against fleas for at least 29 days. The formulation administered to Group 2 longer lasting efficacy above 90% until at least Day 43 and maintained efficacy above 85% until Day 50. The formulation of Group 5 (8% ethyl oleate in DES) exhibited significant efficacy after 12 hours.

Example 8: Efficacy of Spot-on Formulations Comprising Isoxazoline Compound A in Different Carrier Vehicles at 1 mg/Kg Against *Ctenocephalides felis* Fleas in Cats Protected from Grooming In another study, the efficacy of four spot-on formulations comprising Cmpd. A dosed at 1 mg/kg body weight in different carrier vehicles against fleas in cats was studied. Five cats each were allocated to five Treatment Groups: Group 1—Untreated; Group 2—0.833% (w/v) Cmpd. A in dimethylsulfoxide (DMSO); Group 3—0.833% (w/v) Cmpd. A in DMI; Group 4—0.833% (w/v) Cmpd. A in Transcutol®; and Group 5—0.833% (w/v) Cmpd. A in DES. Each cat in the study was fitted with a protective neck collar on Day −1 prior to treatment to prevent the animals from orally ingesting the topically applied formulation while grooming. Cats were infested with approximately 100 *C. felis* on Day −1 and treated on Day 0 with the corresponding spot-on formulation by application of the formulation directly on the skin in the midline of the neck, between the base of the skull and the shoulder blades in a single spot using a 1 mL syringe. Infestations with approximately 100 *C. felis* were conducted weekly on Days 7, 14, 21, 28 and 35. Fleas were removed and counted approximately 24±3 hours following treatment on Day 1 and then on Days 8, 15, 22, 29 and 36. The efficacy for each formulation is presented in Table 10 below.

TABLE 10

Efficacy of Spot-on Formulations Against *Ctenocephalides felis* Fleas in Cats

| Treatment Group | % Reduction | | | | | | |
|---|---|---|---|---|---|---|---|
| | Day 1 | Day 2 | Day 8 | Day 15 | Day 22 | Day 29 | Day 36 |
| Group 2 % Reduction | 43.16 | 60.54 | 98.48 | 95.91 | 97.90 | 90.10 | 74.49 |
| Group 3 % Reduction | 37.90 | 88.97 | 99.62 | 99.32 | 98.80 | 92.66 | 79.54 |
| Group 4 % Reduction | 76.32 | 83.12 | 98.95 | 99.01 | 96.19 | 95.41 | 86.61 |
| Group 5 % Reduction | 54.40 | 82.77 | 98.82 | 99.26 | 99.82 | 92.43 | 88.11 |

Example 9: Long Lasting Efficacy of Spot-on Composition Against *Ctenocephalides felis* Fleas in Cats The efficacy of spot-on compositions comprising Cmpd. A in DMI at different doses against *Ctenocephalides felis* fleas in cats was studied. Four treatment groups were formed with five cats per treatment group: Group 1—untreated control; Group 2—Compound A at 5.0% (w/v) in DMI to deliver a dose of 5 mg/kg; Group 3—Compound A at a concentration of 10.0% (w/v) in DMI to deliver a dose of 10 mg/kg; and Group 4—Compound A at a concentration of 15.0% (w/v) in DMI to deliver a dose of 15 mg/kg. Treatment was administered once on Day 0. The cats were each infested with approximately 100 *C. felis* fleas at each time point evaluated.

Cats in all treatment groups were infested on Days −1, 0 (approx. 12 h following treatment), 7, 28, 49, 70, 91, 105, 119 and 133. Cats were also infested on Days 126 and 140 (Treatment Groups 1 and 2); Days 147, 154, 155, 161, 168 and 175 (Treatment Groups 1, 3 and 4); Days 182, 189 and 197 (Treatment Groups 1 and 4). After each infestation, fleas were removed and counted approximately 48 hours (±3 hours) for most time points.

The results of the study are shown in Tables 11A, 11B and 11C below and in FIG. 1. The study demonstrated surprising long lasting efficacy of the spot-on formulations. The results indicate that formulations comprising Cmpd. A at different concentrations were efficacious compared to Group 1 (untreated control) for extended periods of time. For example Group 2 demonstrated 90% efficacy up to Day 121; Group 3 showed 90% efficacy up to Day 163 and Group 4 exhibited 90% efficacy up to Day 191. This extremely long lasting protection above 90% from one topical application is unpredictable and remarkable.

TABLE 11A

Efficacy of Against *Ctenocephalides felis* Fleas in Cats

| Treatment Group | % Reduction Fleas | | | | | | |
|---|---|---|---|---|---|---|---|
| | Day 0 (12 hr) | Day 2 | Day 9 | Day 30 | Day 51 | Day 72 | Day 93 |
| Group 2 % Reduction | 61.1 | 100.0 | 100.0 | 100.0 | 100.0 | 100.0 | 100.0 |
| Group 3 % Reduction | 95.4 | 100.0 | 100.0 | 100.0 | 100.0 | 100.0 | 100.0 |
| Group 4 % Reduction | 85.3 | 100.0 | 100.0 | 100.0 | 100.0 | 100.0 | 100.0 |

TABLE 11B

Efficacy of Against *Ctenocephalides felis* Fleas in Cats (continued)

| Treatment Group | % Reduction Fleas | | | | | | |
|---|---|---|---|---|---|---|---|
| | Day 107 | Day 121 | Day 128 | Day 135 | Day 142 | Day 149 | Day 155 |
| Group 2 % Reduction | 100.0 | 92.3 | 89.1 | 88.3 | 80.0 | ND | ND |
| Group 3 % Reduction | 100.0 | 100.0 | ND | 99.8 | ND | 99.5 | 50.0 |
| Group 4 % Reduction | 100.0 | 100.0 | ND | 100.0 | ND | 100.0 | 78.0 |

TABLE 11C

Mean Flea Count/% Reduction (continued):

| Treatment Group | % Reduction Fleas | | | | | | |
|---|---|---|---|---|---|---|---|
| | Day 157 | Day 163 | Day 170 | Day 177 | Day 184 | Day 191 | Day 199 |
| Group 2 % Reduction | ND | ND | ND | ND | ND | ND | ND |
| Group 3 % Reduction | 98.1 | 94.5 | 87.8 | 70.8 | ND | ND | ND |
| Group 4 % Reduction | 100.0 | 100.0 | 96.2 | 94.8 | 95.7 | 90.6 | 79.2 |

Example 10: Efficacy of Spot-on Formulations Against *Ixodes ricinus* Ticks in Cats The efficacy of spot-on formulations comprising Cmpd. A were studied against induced infestations of *Ixodes ricinus* ticks in cats. Three treatment groups with six cats per group were randomly allocated: Group 1—Control, untreated; Group 2—Cmpd. A (2.5% w/v in DMI) at 0.1 ml/kg body weight (2.5 mg/kg); and Group 3—Cmpd. A (5.0% w/v in DMI) at 0.1 ml/kg body weight (5 mg/kg). Treatment was administered once on Day 0 and efficacy was assessed based on 48-hour tick (*I. ricinus*) counts following weekly experimental challenge from Day 7 on. As shown in Tables 12A and 12B below, Cmpd. A (2.5% w/v in DMI) at 2.5 mg/kg body weight administered once topically completely prevented the infestation of *I. ricinus* until Day 56 and offered >90% prevention until at least Day 77. In fact, the topical spot-on formulation offered substantial protection against *I. ricinus* ticks until the last day of assessment-Day 93. Due to limitations on tick availability 5 mg/kg was tested only up to Day 44 with 100% efficacy. The excellent long-lasting efficacy of the formulation of the invention against *I. ricinus* ticks in cats is very surprising and unexpected.

TABLE 12A

Efficacy Against *Ixodes ricinus* in Cats

| Treatment Group | % Reduction Ticks | | | | | |
|---|---|---|---|---|---|---|
| | Day 2 | Day 9 | Day 23 | Day 30 | Day 37 | Day 44 |
| Group 2 % Reduction | 23.71 | 100.00 | 99.60 | 100.00 | 99.58 | 100.00 |
| Group 3 % Reduction | 70.27 | 100.00 | 100.00 | 100.00 | 100.00 | 100.00 |

TABLE 12B

Efficacy Against *Ixodes ricinus* in Cats (continued)

| Treatment Group | % Reduction Ticks | | | | | | |
|---|---|---|---|---|---|---|---|
| | Day 51 | Day 58 | Day 65 | Day 72 | Day 79 | Day 86 | Day 93 |
| Group 2 % Reduction | 100.00 | 100.00 | 99.02 | 99.21 | 95.54 | 84.92 | 76.65 |
| Group 3 % Reduction | ND[1] | ND | ND | ND | ND | ND | ND |

[1]ND = not done

Example 11: Efficacy of Spot-on Formulation Containing a Combination of Compound A, Pyriproxyfen and Nitenpyram Against *Ctenocephalides felis* Fleas in Cats The efficacy of three spot-on compositions comprising a combination of Compound A, pyriproxyfen and nitenpyram against *Ctenocephalides felis* fleas in cats was studied and compared with an untreated control and with a spot-on composition comprising nitenpyram alone. Cats were allocated into five Treatment Groups with 5 cats per group: Group 1—cats were untreated (control); Group 2—cats were treated spot-on solution containing 0.83% (w/v) Compound A, 2.08% (w/v) nitenpyram, and 4.17% (w/v) pyriproxyfen in Transcutol® to deliver doses of 1.0 mg/kg Compound A, 2.5 mg/kg nitenpyram and 5.0 mg/kg pyriproxyfen; Group 3—cats were treated a spot-on solution containing 0.83% (w/v) Compound A, 4.17% (w/v) nitenpyram, and 4.17% (w/v) pyriproxyfen in Transcutol® to deliver doses of 1.0 mg/kg Compound A, 5.0 mg/kg nitenpyram and 5.0 mg/kg pyriproxyfen; Group 4—cats were treated with a spot-on composition containing 0.83% (w/v) Compound A, 8.33% (w/v) nitenpyram and 4.17% (w/v) pyriproxyfen in Transcutol® to deliver doses of 1.0 mg/kg Compound A, 10.0 mg/kg nitenpyram and 5.0 mg/kg pyriproxyfen; Group 5—cats were treated with a spot-on composition containing 2.08% (w/v) nitenpyram alone in Transcutol® to deliver a dose of 5.0 mg/kg body weight.

Treatment was administered once on Day 0. The cats were each infested with approximately 100 *C. felis* fleas at day −1, on Day 0 approximately 12 hours post treatment and then on Days 1 (approx. 24 hours post treatment), 2, 7, 14, 21, 28 and 35. After each infestation, fleas were removed and counted approximately 12 hours (±3) on Day 0, and then on Days 1, 2, 8, 15, 22, 29 and 36 (24±3 hours after infestation).

The results of the study are shown in Table 13 below. The study demonstrated that a spot-on composition comprising a combination of an isoxazoline compound (Compound A), a neonicotinoid (nitenpyram) and an insect growth regulator (pyriproxyfen) exhibits extremely fast acting and long-lasting efficacy.

TABLE 13

Efficacy of Spot-on Formulation Comprising Three Active Agents Against *Ctenocephalides felis* Fleas in Cats

| Treatment Group | % Reduction | | | | | |
|---|---|---|---|---|---|---|
| | Day 0 (12 h) | Day 1 (24 h) | Day 2 (24 h) | Day 8 (24 h) | Day 15 (24 h) | Day 22 (24 h) |
| Group 2 % Reduction | 99.17 | 100.00 | 100.00 | 100.00 | 100.00 | 98.76 |

TABLE 13-continued

Efficacy of Spot-on Formulation Comprising Three
Active Agents Against *Ctenocephalides felis* Fleas in Cats

| | % Reduction | | | | | |
|---|---|---|---|---|---|---|
| Treatment Group | Day 0 (12 h) | Day 1 (24 h) | Day 2 (24 h) | Day 8 (24 h) | Day 15 (24 h) | Day 22 (24 h) |
| Group 3 % Reduction | 99.59 | 99.22 | 99.78 | 100.00 | 99.51 | 97.71 |
| Group 4 % Reduction | 97.69 | 100.00 | 100.00 | 100.00 | 100.00 | 98.08 |
| Group 5 % Reduction | 99.44 | 99.79 | 100.00 | 100.00 | 96.76 | 93.63 |

Example 12: Efficacy of Spot-on Compositions Comprising Compound A Against *Otodectes Cynotis* (Ear Mites) in Cats The efficacy of two spot-on compositions comprising Compound A at doses of 5 mg/kg and 10 mg/kg against *Otodectes cynotis* in cats was evaluated compared to an untreated control. Eighteen healthy cats were grouped into three study groups consisting of six cats per group. Cats in the treatment groups were infested with *Otodectes cynotis* obtained from naturally infested donor cats prior to acclimation on Day −7. Group 1 was an untreated control group. Cats in Groups 2 and 3 were treated once on Day 0 with a spot-on composition comprising Compound A at two different concentrations and doses by application of the formulation directly on the skin in the midline of the neck between the base of the skull and the shoulder blades with a 1 mL disposable syringe. Cats in Group 2 were treated with a spot-on composition containing 5.0% (w/v) Compound A in a carrier containing 40% (v/v) diethyl sebacate (DES) in dimethylisosorbide (DMI) at a dose of 5 mg/kg body weight; and cats in Group 3 were treated with a spot-on composition containing 10.0% (w/v) Compound A in a carrier containing 40% (v/v) DES in DMI at a dose of 10 mg/kg body weight. Assessment of the ear mite infestation by otoscopic examination was performed on all cats on Days −7, 3, 7 and 14. Visible live ear mites (adult or immature) were counted and debris/cerumen level was estimated for both ear ducts. A quantitative assessment of ear mites by ear duct flushing, mite collection and live mite count was performed on Day 14. Relative to the untreated control, Group 2 reduced the infestation of ear mites by 99.0% (only one mite found) and Group 3 reduced the infestation of ear mites by 100.0% (no live mites found in any cat).

Example 13: Efficacious Plasma Concentration for Topical Compositions

Plasma concentrations of Compound A from dogs in the studies of Examples 1 and 4 were determined according to the description in Example 1, and the plasma concentration versus % efficacy against *A. americanum* and *D. variabilis* were fit to a Sigmoidal Emax model. The $EC_{90}$ (concentration required to achieve 90% efficacy) against *A. americanum* and *D. variabilis* ticks were determined to be 92 ng/mL and 70 ng/mL, respectively. Using a similar approach, the $EC_{90}$ for *R. sanguineus* ticks from a separate study was found to be 69 ng/mL. For comparison, the $EC_{90}$ values from an oral dosage form against *A. americanum, D. variabilis* and *R. sanguineus* ticks was found to be 158 ng/mL, 110 ng/mL and 101 ng/mL, respectively. Since Compound A is systemically active, the lower concentration of the compound in the plasma required to achieve 90% efficacy from the topical compositions of the invention is surprising and unexpected.

Example 14: Efficacy of Pour-on Formulation Against *Haematobia irritans* (Horn Fly) in Cattle The efficacy of a pour-on formulation of the invention comprising isoxazoline Compound A was tested and compared with an untreated control. Two healthy, female Angus crossbread cattle of one year of age weighing between 224 to 330 kg were used in each study group. Cattle in Group 1 were untreated (control) and cattle in Group 2 were treated with a pour-on formulation comprising Compound A at a concentration of 10% (w/v) in DES at a dose of 1 ml/10 kg once on Day 0. The formulation was applied by measuring the required amount of the solution into a marked disposable syringe and applying the material evenly along the mid-line of the back of each animal from the withers to the tail head. Each animal was infested with approximately 200 horn flies released into each of the animal rooms on Day 1, approximately 24 hours post treatment. Approximately 200 horn flies were released again on Days 7, 14, 21, 28 and 36. Horn fly counts were performed at 5 hours and 24 hours after each infestation. Tables 14A and 14B below show the efficacy of the pour-on formulation of the invention.

TABLE 14A

Efficacy of Pour-on Formulation Against Horn Fly

| | % Reduction | | | | | |
|---|---|---|---|---|---|---|
| Treatment Group[1] | Day 1 (5 h) | Day 2 (24 h) | Day 7 (5 h) | Day 8 (24 h) | Day 14 (5 h) | Day 15 (24 h) |
| Group 2 % Reduction | 81.2 | 99.6 | 84.2 | 99.7 | 89.5 | 99.2 |

TABLE 14B

Efficacy of Pour-on Formulation Against Horn Fly (Continued)

| | % Reduction | | | | | |
|---|---|---|---|---|---|---|
| Treatment Group[1] | Day 21 (5 h) | Day 22 (24 h) | Day 28 (5 h) | Day 29 (24 h) | Day 35 (5 h) | Day 36 (24 h) |
| Group 2 % Reduction | 67.6 | 97.4 | 11.7 | 90.4 | 42.6 | 90.4 |

As the tables 14A and 14B show, significant efficacy against horn flies was observed after only 5 hours post infestation. Efficacy of at least 90% was observed 24 hours after infestation through the end of the study (day 36).

Example 15: Efficacy of Pour-on Formulation Against *Rhipicephalus* (*Boophilus*) *Microplus* Ticks The efficacy of two pour-on formulations of the invention comprising Compound A at doses of 2.5 mg/kg and 10 mg/kg were tested against infestations of *Rhipicephalus* (*Boophilus*) *microplus* ticks compared with an untreated control. Five healthy head of cattle of 6 to 15 months of age weighing between 100 to 200 kg were used in each study group. Cattle in Group 1 were untreated (control). Cattle in Group 2 were treated on Day 0 with a pour-on formulation comprising Compound A at a concentration of 2.5% (w/v) in DES at a dose of 2.5 mg/kg; and cattle in Group 3 were treated on Day 0 with a pour-on formulation comprising Compound A at a concentration of 10% (w/v) in DES at a dose of 10 mg/kg. Several weeks before treatment, cattle are infested three times a week with approximately 2500 *Rhipicephalus* (*Boophilus*) *microplus* larvae to establish ongoing infestations. Cattle in Groups 2 and 3 were treated with the respective compositions on Day 0 by measuring the required amount of the solution into a marked disposable syringe and applying the material evenly along the mid-line of the back of each animal from the withers to the tail head.

Each animal was challenged by infestation with approximately 5000 *R. microplus* larvae on Days 7 and 21 and every 14 days thereafter. Ticks dropping from each animal in the previous 24 hours were collected daily and counted from Day 1 until the end of the study. Since the life cycle of the ticks from the point of infestation with larvae until engorged ticks fall off is approximately 21 days (average), the assessment of efficacy for the challenges on Days 7 and 21 and every 14 days thereafter, was done for a range of 7 or 8 days starting approximately 21 days after the challenge. The assessment of efficacy at the beginning of the study was done from day 1 until Day 21.

Figure 2:
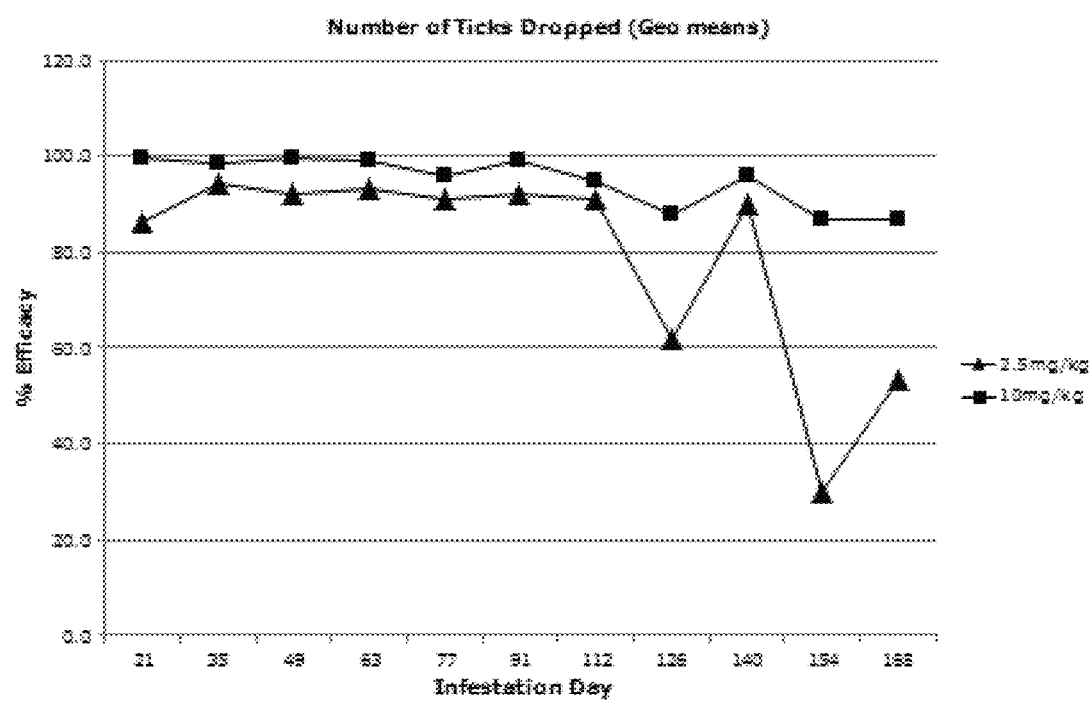
FIG. 2 is a plot showing the long lasting efficacy of a pour-on composition comprising Compound A against *Rhipicephalus* (*Boophilus*) *microplus* in cattle based on the number of ticks dropped (Example 15).
Figure 3:
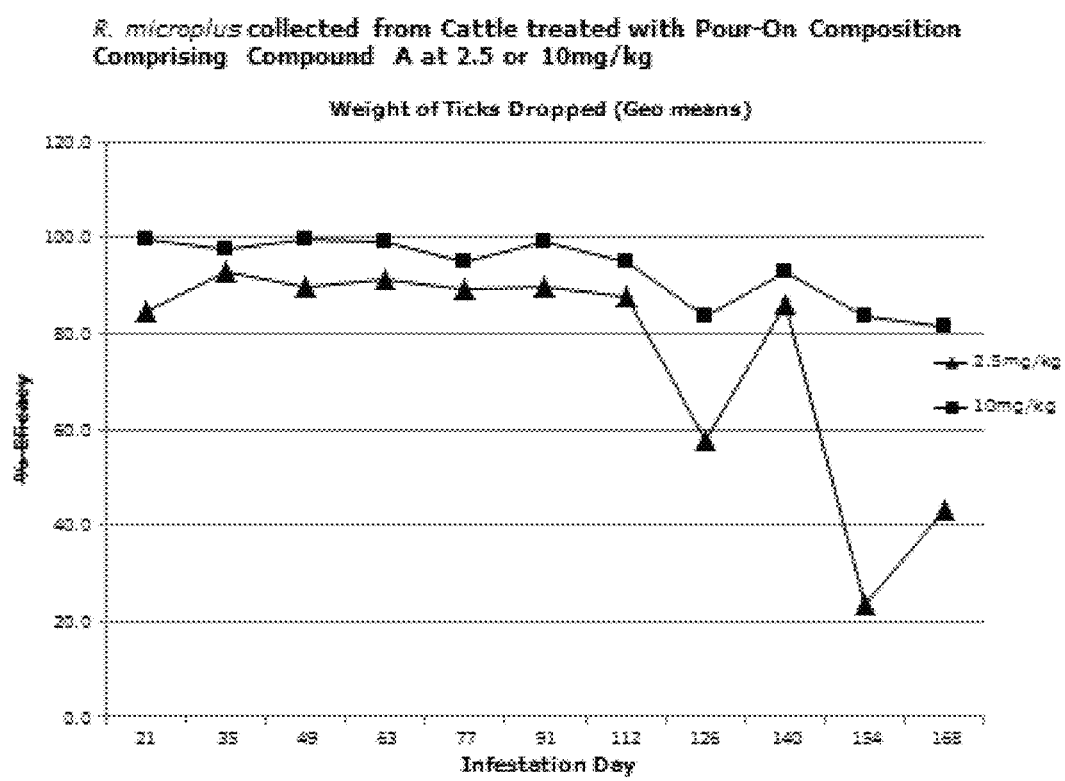
FIG. 3 is a plot showing the long lasting efficacy of a pour-on composition comprising Compound A against *Rhipicephalus* (*Boophilus*) *microplus* in cattle based on the weight of ticks that drop (Example 15).

In addition, the ticks collected were weighed as a group to measure the impact of the treatment on the weight gain of the ticks compared to the control to assess the vitality and reproductive capability of the treated ticks. Tables 15A and 15B below shows the total tick count % efficacy of the two pour-on formulations against *R. microplus* through 139 days post treatment compared with an untreated control group. Tables 16A and 16B show the % efficacy of the two pour-on formulations based on the weight of the ticks collected. FIGS. 2 and 3 shows plots of the % efficacy of the two formulations based on total tick counts and total weight, respectively. As evidenced from the tables and the figures, the pour-on formulations of the invention at both 2.5 mg/kg and 10 mg/kg provide excellent efficacy against *Rhipicephalus* (*Boophilus*) *microplus* ticks for an extended period of time. The pour-on compositions exhibited tick count efficacy above 90% for at least day 139 after administration of the composition. Furthermore, as shown in Tables 16A and 16B, the two pour-on compositions were extremely effective against ticks based on the weight of the ticks collected. This data shows that the compositions were highly effective at inhibiting the reproductive capability of the ticks for an extended duration of time. The extremely long lasting efficacy above 90% for pour-on composition against *Rhipicephalus* (*Boophilus*) *microplus* ticks is remarkable compared with pour-on formulations known in the art.

TABLE 15A

Tick Count Efficacy Against *Rhipicephalus* (*Boophilus*) *microplus*

| Treatment Group | Average % Efficacy (Tick Count) | | | | | | |
|---|---|---|---|---|---|---|---|
| | Day 1-21 | Day 28-34 | Day 41-48 | Day 55-62 | Day 69-76 | Day 83-90 | Day 97-104 |
| Challenge Day | | 7 | 21 | 35 | 49 | 63 | 77 |
| Group 2 % Efficacy | 58.8 | 75.6 | 77.0 | 91.2 | 88.3 | 90.7 | 79.8 |
| Group 3 % Efficacy | 78.1 | 92.0 | 98.0 | 97.8 | 99.3 | 98.9 | 92.4 |

TABLE 15B

Tick Count Efficacy Against *Rhipicephalus* (*Boophilus*) *microplus*

| Treatment Group | Average % Efficacy (Tick Count) | | | |
|---|---|---|---|---|
| | Day 111-118 | Day 132-139 | Day 146-153 | Day 160-167 |
| Challenge Day | 91 | 112 | 126 | 140 |
| Group 2 % Efficacy | 79.0 | 86.2 | 30.3 | 74.0 |
| Group 3 % Efficacy | 96.6 | 92.4 | 72.4 | 85.8 |

TABLE 16A

Tick Weight Efficacy Against *Rhipicephalus* (*Boophilus*) *microplus*

| Treatment Group | Average % Efficacy (Tick Weight) | | | | | | |
|---|---|---|---|---|---|---|---|
| | Day 1-21 | Day 28-34 | Day 41-48 | Day 55-62 | Day 69-76 | Day 83-90 | Day 97-104 |
| Challenge Day | | 7 | 21 | 35 | 49 | 63 | 77 |
| Group 2 % Efficacy | 69.1 | 81.8 | 72.9 | 87.7 | 84.8 | 87.4 | 76.0 |
| Group 3 % Efficacy | 85.4 | 95.2 | 98.3 | 96.6 | 99.2 | 98.6 | 90.2 |

TABLE 16B

Tick Weight Efficacy Against *Rhipicephalus* (*Boophilus*) *microplus*

| Treatment Group | Average % Efficacy (Tick Weight) | | | |
|---|---|---|---|---|
| | Day 111-118 | Day 132-139 | Day 146-153 | Day 160-167 |
| Challenge Day | 91 | 112 | 126 | 140 |
| Group 2 % Efficacy | 74.0 | 83.2 | 20.6 | 63.4 |
| Group 3 % Efficacy | 96.0 | 92.4 | 61.4 | 76.3 |

Example 16: Efficacy of Pour-on Formulation Against *Linognathus vituli* (Sucking Lice) in Cattle The efficacy of two pour-on formulations of the invention comprising isoxazoline Compound A at doses of 2.5 mg/kg and 10 mg/kg were tested against natural and induced infestations with *Linognathus vituli* (sucking lice) in cattle compared with an untreated control. Four healthy head of cattle weighing between 100 to 300 kg were used in each study group. Cattle in Group 1 were untreated (control). Cattle in Group 2 were treated on Day 0 with a pour-on formulation comprising Compound A at a concentration of 2.5% (w/v) in DES at a dose of 2.5 mg/kg; and cattle in Group 3 were treated on Day 0 with a pour-on formulation comprising Compound A at a concentration of 10% (w/v) in DES at a dose of 10 mg/kg. The formulation was applied by measuring the required amount of the solution into a marked disposable syringe and applying the material evenly along the mid-line of the back of each animal from the withers to the tail head.

Live lice (adults plus nymphs) were counted on days 2, 7, 14, 21, 28, 35, 42, 49 and 56 by counting lice on six selected sites approximately 5 cm×15 cm on the body surface of the animal by direct examination. In the absence of lice on the selected sites, a thorough body search was conducted. The total louse counts per animal were determined by summation of the live louse numbers at each site per animal. Tables 17A and 17B below show the efficacy of the two pour-on formulations against *Linognathus vituli* over 56 days. As the tables show, both pour-on formulations were efficacious through at least day 56 of the study with 100% efficacy observed starting day 7. Efficacy on day 2 of the study was greater than 90% in each of the study groups. The long lasting efficacy against *Linognathus vituli* from one topical treatment is unexpected and surprising.

TABLE 17A

Efficacy of Pour-on Formulation Against *Linognathus vituli*

| | % Reduction | | | | |
|---|---|---|---|---|---|
| Treatment Group[1] | Day 2 | Day 7 | Day 14 | Day 21 | Day 28 |
| Group 2 % Reduction | 92 | 100 | 100 | 100 | 100 |
| Group 3 % Reduction | 98 | 100 | 100 | 100 | 100 |

TABLE 17B

Efficacy of Pour-on Formulation Against *Linognathus vituli* (continued)

| | % Reduction | | | |
|---|---|---|---|---|
| Treatment Group | Day 35 | Day 42 | Day 49 | Day 56 |
| Group 2 % Reduction | 92 | 100 | 100 | 100 |
| Group 3 % Reduction | 98 | 100 | 100 | 100 |

Example 17: Efficacy of Pour-on Formulation Against *Sarcoptes scabiei* Var. Bovis (Mange Mites) in Cattle The efficacy of two pour-on formulations of the invention comprising isoxazoline Compound A at doses of 2.5 mg/kg and 10 mg/kg were tested against natural and induced infestations with *Sarcoptes scabiei* var. *bovis* (mange mites) in cattle compared with an untreated control. Four healthy head of cattle weighing between 100 to 300 kg were used in each study group. Cattle in Group 1 were untreated (control). Cattle in Group 2 were treated on Day 0 with a pour-on formulation comprising Compound A at a concentration of 2.5% (w/v) in DES at a dose of 2.5 mg/kg; and cattle in Group 3 were treated on Day 0 with a pour-on formulation comprising Compound A at a concentration of 10% (w/v) in DES at a dose of 10 mg/kg. The formulation was applied by measuring the required amount of the solution into a marked disposable syringe and applying the material evenly along the mid-line of the back of each animal from the withers to the tail head.

Live (motile) *Sarcoptes scabiei* var. *bovis* (mange mites) were counted on days 7, 14, 20, 27, 34, 41, 48 and 55 in scrapings collected from the edges of active lesions or, if lesions regressed during the study, from the area where active lesions were at the commencement of the study. Scrapings were made from six sites with an area of at least 3 cm×3 cm in size on each animal. Tables 18A and 18B below show the efficacy of the two pour-on formulations against *Sarcoptes scabiei* var. *bovis* over 56 days. As the data shows, both pour-on formulations were efficacious through at least day 56 of the study with efficacy of higher than 95% starting on day 7. The efficacy of the 10% (w/v) formulation exhibited an efficacy of 100% from day 14 through day 55, while the efficacy of the lower concentration pour-on formulation (Group 2) showed 100% starting from day 27 through the end of the study. The long lasting efficacy of the pour-on formulations of the invention against *Sarcoptes scabiei* var. *bovis* from one topical treatment is unexpected and surprising.

TABLE 18A

Efficacy of Pour-on Formulation Against *Sarcoptes scabiei* var. *bovis*

| | % Reduction | | | |
|---|---|---|---|---|
| Treatment Group | Day 7 | Day 14 | Day 20 | Day 27 |
| Group 2 % Reduction | 96.7 | 98.2 | 99.6 | 100 |
| Group 2 % Reduction | 96.8 | 100 | 100 | 100 |

TABLE 18B

Efficacy of Pour-on Formulation Against *Sarcoptes scabiei* var. *bovis* (continued)

| | % Reduction | | | |
|---|---|---|---|---|
| Treatment Group | Day 34 | Day 41 | Day 48 | Day 55 |
| Group 2 % Reduction | 100 | 100 | 100 | 100 |
| Group 2 % Reduction | 100 | 100 | 100 | 100 |

As the non-limiting examples above demonstrate, the compositions of the invention comprising at least one isoxazoline active agent show superior long lasting efficacy against ectoparasites in a mammal (e.g. dogs, cats and cattle).

The invention is further described by the following numbered paragraphs:

1. A topical veterinary composition for treating or preventing a parasitic infection or infestation in an animal comprising:

a) at least one isoxazoline active agent of Formula (I):

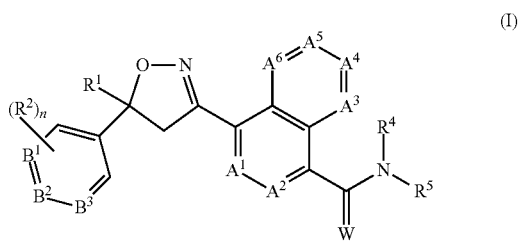

wherein:

$A^1, A^2, A^3, A^4, A^5$ and $A^6$ are independently selected from the group consisting of $CR^3$ and N, provided that at most 3 of $A^1, A^2, A^3, A^4, A^5$ and $A^6$ are N;

$B^1, B^2$ and $B^3$ are independently selected from the group consisting of $CR^2$ and N;

W is O or S;

R$^1$ is C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl or C$_4$-C$_7$ cycloalkylalkyl, each optionally substituted with one or more substituents independently selected from R$^6$;

each R$^2$ is independently H, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_1$-C$_6$ alkylamino, C$_2$-C$_6$ dialkylamino, C$_2$-C$_4$ alkoxycarbonyl, —CN or —NO$_2$;

each R$^3$ is independently H, halogen, C$_1$-C$_6$ alkyl, C$_1$-C$_6$ haloalkyl, C$_3$-C$_6$ cycloalkyl, C$_3$-C$_6$ halocycloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_1$-C$_6$ alkylamino, C$_2$-C$_6$ dialkylamino, —CN or —NO$_2$;

R$^4$ is H, C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl, C$_4$-C$_7$ cycloalkylalkyl, C$_2$-C$_7$ alkylcarbonyl or C$_2$-C$_7$ alkoxycarbonyl;

R$^5$ is H, OR$^{10}$, NR$^{11}$R$^{12}$ or Q$^1$; or C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl or C$_4$-C$_7$ cycloalkylalkyl, each optionally substituted with one or more substituents independently selected from R$^7$; or R$^4$ and R$^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of C$_1$-C$_2$ alkyl, halogen, —CN, —NO$_2$ and C$_1$-C$_2$ alkoxy;

each R$^6$ is independently halogen, C$_1$-C$_6$ alkyl, C$_1$-C$_6$ alkoxy, C$_1$-C$_6$ alkylthio, C$_1$-C$_6$ alkylsulfinyl, C$_1$-C$_6$ alkylsulfonyl, —CN or —NO$_2$;

each R$^7$ is independently halogen; C$_1$-C$_6$ alkyl, C$_3$-C$_6$ cycloalkyl, C$_1$-C$_6$ alkoxy, C$_1$-C$_6$ alkylthio, C$_1$-C$_6$ alkylsulfinyl, C$_1$-C$_6$ alkylsulfonyl, C$_1$-C$_6$ alkylamino, C$_2$-C$_8$ dialkylamino, C$_3$-C$_6$ cycloalkylamino, C$_2$-C$_7$ alkylcarbonyl, C$_2$-C$_7$ alkoxycarbonyl, C$_2$-C$_7$ alkylaminocarbonyl, C$_3$-C$_9$ dialkylaminocarbonyl, C$_2$-C$_7$ haloalkylcarbonyl, C$_2$-C$_7$ haloalkoxycarbonyl, C$_2$-C$_7$ haloalkylaminocarbonyl, C$_3$-C$_9$ dihaloalkylaminocarbonyl, hydroxy, —NH$_2$, —CN or —NO$_2$; or Q$^2$;

each R$^8$ is independently halogen, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_1$-C$_6$ alkylamino, C$_2$-C$_6$ dialkylamino, C$_2$-C$_4$ alkoxycarbonyl, —CN or —NO$_2$;

each R$^9$ is independently halogen, C$_1$-C$_6$ alkyl, C$_1$-C$_6$ haloalkyl, C$_3$-C$_6$ cycloalkyl, C$_3$-C$_6$ halocycloalkyl, C$_1$-C$_6$ alkoxy, C$_1$-C$_6$ haloalkoxy, C$_1$-C$_6$ alkylthio, C$_1$-C$_6$ haloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_1$-C$_6$ alkylamino, C$_2$-C$_6$ dialkylamino, —CN, —NO$_2$, phenyl or pyridinyl;

R$^{10}$ is H; or C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl or C$_4$-C$_7$ cycloalkylalkyl, each optionally substituted with one of more halogen;

R$^{11}$ is H, C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl, C$_4$-C$_7$ cycloalkylalkyl, C$_2$-C$_7$ alkylcarbonyl or C$_2$-C$_7$ alkoxycarbonyl;

R$^{12}$ is H; Q$^3$; or C$_1$-C$_6$ alkyl, C$_2$-C$_6$ alkenyl, C$_2$-C$_6$ alkynyl, C$_3$-C$_6$ cycloalkyl, C$_4$-C$_7$ alkylcycloalkyl or C$_4$-C$_7$ cycloalkylalkyl, each optionally substituted with one or more substituents independently selected from R$^7$; or R$^{11}$ and R$^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of C$_1$-C$_2$ alkyl, halogen, —CN, —NO$_2$ and C$_1$-C$_2$ alkoxy;

Q$^1$ is a phenyl ring, a 5- or 6-membered heterocyclic ring, or an 8-, 9- or 10-membered fused bicyclic ring system optionally containing one to three heteroatoms selected from up to 1 O, up to 1 S and up to 3 N, each ring or ring system optionally substituted with one or more substituents independently selected from R$^8$;

each Q$^2$ is independently a phenyl ring or a 5- or 6-membered heterocyclic ring, each ring optionally substituted with one or more substituents independently selected from R$^9$;

Q$^3$ is a phenyl ring or a 5- or 6-membered heterocyclic ring, each ring optionally substituted with one or more substituents independently selected from R$^9$; and n is 0, 1 or 2; and b) a pharmaceutically acceptable carrier that is suitable for application to the skin of an animal; and wherein the carrier does not comprise glycofurol and is not a binary mixture of propylene glycol and glycerol formal.

2. The topical veterinary composition of paragraph 1, wherein in the isoxazoline active agent of Formula (I):

W is O;

R$^4$ is H or C$_1$-C$_6$ alkyl;

R$^5$ is —CH$_2$C(O)NHCH$_2$CF$_3$;

each of A$^1$, A$^2$, A$^3$, A$^4$, A$^5$ and A$^6$ is CH;

R$^1$ is C$_1$-C$_6$ alkyl each optionally substituted with one or more substituents independently selected from R$^6$;

R$^6$ is halogen or C$_1$-C$_6$ alkyl; and

B$^1$, B$^2$, and B$^3$ are independently CH, C-halogen, C—C$_1$-C$_6$ alkyl, C—C$_1$-C$_6$ haloalkyl, or C—C$_1$-C$_6$ alkoxy.

3. The topical veterinary composition of paragraph 1, wherein in the isoxazoline active agent of Formula (I):

W is O;

R$^1$ is CF$_3$;

B$^2$ is CH;

B$^1$ is chloro;

B$^3$ is CF$_3$;

each of A$^1$, A$^2$, A$^3$, A$^4$, A$^5$ and A$^6$ is CH;

R$^4$ is H; and

R$^5$ is —CH$_2$C(O)NHCH$_2$CF$_3$.

4. The topical veterinary composition of paragraph 1, wherein the pharmaceutically acceptable carrier comprises a diester of a dicarboxylic acid, a glycol ester, a glycol ether, a fatty acid ester, a polyethylene glycol, or polyethylene glycol ester, an oil, an alcohol, a glycerol ester, a glycerol ether, propylene glycol, ethylene glycol, a glycol carbonate, dimethyl isosorbide, N-methylpyrrolidone, or a mixture thereof.

5. The topical veterinary composition of paragraph 4, wherein the diester of a dicarboxylic acid is a diester of a C$_6$-C$_{16}$ dicarboxylic acid.

6. The topical veterinary composition of paragraph 5, wherein the diester of a C$_6$-C$_{16}$ dicarboxylic acid is diethyl sebacate or diisopropyl adipate.

7. The topical veterinary composition of paragraph 4, wherein the pharmaceutically acceptable carrier comprises mixture of a diester of a dicarboxylic acid and a propylene glycol ester, a fatty acid ester, a polyethylene glycol ester, a polyethylene glycol, an oil, a C$_6$-C$_{20}$ long-chain aliphatic alcohol, a C$_1$-C$_8$ alcohol, glycol ether, or a combination thereof.

8. The topical veterinary composition of paragraph 4, wherein the pharmaceutically acceptable carrier comprises a mixture of a diester of a dicarboxylic acid and further comprises a mixed ester of sucrose and acetic and isobutyric acid, a low melting wax, a hard fat or a block co-polymer of ethylene oxide and propylene oxide, or a combination thereof.

9. The topical veterinary composition of paragraph 4, wherein the pharmaceutically acceptable carrier comprises dimethyl isosorbide, glycerol formal, propylene carbonate, triacetin, diethyleneglycol monoethyl ether, polyethylene glycol 400 or benzyl alcohol, or a mixture thereof.

10. The topical veterinary composition of any one of paragraph 1 to 9, wherein the composition further comprises at least a second active agent.

11. The topical veterinary composition of paragraph 10, wherein the at least second active agent is an insect growth regulator, a neonicotinoid or an avermectin or milbemycin.

12. The topical veterinary composition of paragraph 11, wherein the isoxazoline active agent is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide and the neonicotinoid is nitenpyram.

13. The topical veterinary composition of paragraph 11, wherein the at least second active agent is an insect growth regulator.

14. The topical veterinary composition of paragraph 13, wherein the insect growth regulator is (S)-methoprene, pyriproxyfen, hydroprene, cyromazine, fluazuron, lufenuron, or novaluron.

15. The topical veterinary composition of paragraph 11, wherein the avermectin or milbemycin is eprinomectin, ivermectin, selamectin, milbemectin, milbemycin D, milbemycin oxime, or moxidectin 16. The topical veterinary composition of paragraph 10, wherein the at least second active agent is an anthelmintic active agent selected from thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, or an aryloazol-2-yl cyanoethylamino active agent.

17. The topical veterinary composition of any one of paragraph 1 to 16, wherein the composition is a spot-on composition.

18. The topical veterinary composition of any one of paragraph 1 to 16, wherein the composition is a pour-on composition.

19. A method for the treatment or prevention of a parasitic infestation or infection in an animal comprising administering to the animal an effective amount of the topical veterinary composition of any of paragraph 1 to 18.

20. The method of paragraph 19, wherein the isoxazoline is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

21. Use of an isoxazoline of formula (I) in paragraph 1 in the preparation of a topical veterinary composition for the treatment or protection of an animal against parasites.

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for the treatment or prevention of a parasitic infestation or infection in an animal comprising administering to the animal an effective amount of a spot-on topical veterinary composition comprising:

a) at least one isoxazoline active agent of Formula (I):

wherein:
$A^1$, $A^2$, $A^3$, $A^4$, $A^5$ and $A^6$ are each CH;
$B^1$ and $B^3$ are independently $CR^2$;
$B^2$ is CH;
W is O;
$R^1$ is $CF_3$;
each $R^2$ is independently halogen or $C_1$-$C_3$-haloalkyl;
$R^4$ is H;
$R^5$ is $C_1$-$C_4$alkyl substituted with $R^7$;
$R^7$ is $C_2$-$C_7$ alkylaminocarbonyl, $C_3$-$C_9$ dialkylaminocarbonyl, $C_2$-$C_7$ haloalkylaminocarbonyl or $C_3$-$C_9$ dihaloalkylaminocarbonyl;
and
n is 2; and b) a pharmaceutically acceptable carrier that is suitable for the application to the skin of an animal; and wherein the carrier comprises dimethyl isosorbide;
wherein the volume of the spot-on composition is from about 0.1 ml to about 5 ml and the isoxazoline active agent of Formula (I) is present in the composition in a concentration of about 0.5 to about 25% (w/v); and wherein the method has an efficacy of at least about 90% against fleas for at least about 1 month.

2. The method of claim 1, wherein the isoxazoline is 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide.

3. The method of claim 1, wherein:
$R^5$ is —$CH_2C(O)NHCH_2CF_3$;
$B^1$ and $B^3$ are independently C—Cl, C—F or C—$CF_3$.

4. The method of claim 1, wherein the pharmaceutically acceptable carrier further comprises a diester of a dicarboxylic acid, a glycol ester, a glycol ether, a polyglycol ether, a fatty acid ester, a polyethylene glycol, polyethylene glycol ester, an oil, an alcohol, a glycerol ester, a glycerol ether, propylene glycol, ethylene glycol, a glycol carbonate or N-methylpyrrolidone, or a mixture thereof.

5. The method of claim 4, wherein the diester of a dicarboxylic acid is a diester of a $C_6$-$C_{16}$ dicarboxylic acid.

6. The method of claim 5, wherein the diester of a $C_6$-$C_{16}$ dicarboxylic acid is diethyl sebacate or diisopropyl adipate.

7. The method of claim 4, wherein the pharmaceutically acceptable carrier comprises a propylene glycol ester, a fatty acid ester, a polyethylene glycol ester, a polyethylene glycol, an oil, a $C_6$-$C_{20}$ long-chain aliphatic alcohol, a $C_1$-$C_8$ alcohol or a glycol ether, or a combination thereof.

8. The method of claim 1, wherein the pharmaceutically acceptable carrier further comprises a mixed ester of sucrose and acetic acid and isobutyric acid, a low melting wax, a hard fat or a block co-polymer of ethylene oxide and propylene oxide, or a combination thereof.

9. The method of claim 4, wherein the pharmaceutically acceptable carrier comprises glycerol formal, propylene carbonate, triacetin, diethyleneglycol monoethyl ether, polyethylene glycol 400 or benzyl alcohol, or a mixture thereof.

10. The method of claim 1, further comprising one or more additional active agent(s).

11. The method of claim 10, wherein the one or more additional active agent(s) is an insect growth regulator, a neonicotinoid, an avermectin, a milbemycin, a pyrethroid, a phenylpyrazole, praziquantel or a depsipeptide, or a mixture thereof.

12. The method of claim 11, wherein the additional active agent is a neonicotinoid, and wherein the neonicotinoid is nitenpyram or imidacloprid.

13. The method of claim 11, wherein the additional active agent is an insect growth regulator.

14. The method of claim 13, wherein the insect growth regulator is (S)-methoprene, pyriproxyfen, hydroprene, cyromazine, fluazuron, lufenuron, or novaluron.

15. The method of claim 11, wherein the additional active agent is an avermectin, and wherein the avermectin is eprinomectin, ivermectin or selamectin.

16. The method of 10, wherein the additional active agent is selected from the group consisting of thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, and an aryloazol-2-yl cyanoethyl-amino active agent.

17. The method of claim 11, wherein the additional active agent is a pyrethroid, and wherein the pyrethroid is permethrin.

18. The method of claim 11, wherein the additional active agent is a phenylpyrazole, and wherein the phenylpyrazole is fipronil.

19. The method of claim 11, wherein the additional active agent is a depsipeptide, and wherein the depsipeptide is emodepside.

20. The method of claim 9, wherein the pharmaceutically acceptable carrier comprises a mixture of dimethyl isosorbide and glycerol formal.

21. The method of claim 7, wherein the pharmaceutically acceptable carrier comprises a mixture of dimethyl isosorbide and a fatty acid ester.

22. The method of claim 4, wherein the pharmaceutically acceptable carrier comprises a mixture of dimethyl isosorbide and a polyglycol ether.

23. The method of claim 4, wherein the pharmaceutically acceptable carrier comprises a glycol ether selected from the group consisting of butyl diglycol, propylene glycol monomethyl ether, propylene glycol monoethyl ether, dipropylene glycol n-butyl ether, ethylene glycol monoethyl ether, ethylene glycol monomethyl ether, dipropylene glycol monomethyl ether, and diethylene glycol monomethyl ether.

24. The method of claim 1 or 20, wherein the isoxazoline active agent of formula (I) is present in a concentration of about 1 to about 10% (w/v).

25. The method of claim 1 or 20, wherein the isoxazoline active agent of formula (I) is present in a concentration of about 1 to about 5% (w/v).

26. The method of claim 1 or 20, wherein the isoxazoline active agent of formula (I) is present in a concentration of about 0.5 to about 2.0% (w/v).

27. The method of claim 11, wherein the one or more additional active agent(s) is a milbemycin, and wherein the milbemycin is moxidectin or milbemycin oxime.

28. The method of claim 11, wherein the one or more additional active agent(s) is a combination of an avermectin and praziquantel or a combination of a milbemycin and praziquantel, and wherein in the isoxazoline active agent of formula (I):

W is O;
$R^1$ is $CF_3$;
$B^2$ is CH;
$B^1$ is C—Cl;
$B^3$ is C—$CF_3$;
Each of $A^1$, $A^2$, $A^3$, $A^4$, $A^5$ and $A^6$ is CH;
$R^4$ is H; and
$R^5$ is —$CH_2C(O)NHCH_2CF_3$.

29. The method of claim 28, wherein the avermectin is eprinomectin.

30. The method of claim 28, wherein the milbemycin is moxidectin.

31. The method of claim 29 or 30, wherein the isoxazoline active agent of formula (I) is present in a concentration of about 1 to about 10% (w/v).

32. The method of claim 29 or 30, wherein the isoxazoline active agent of formula (I) is present in a concentration of about 1 to about 5% (w/v).

33. The method of claim 29 or 30, wherein the isoxazoline active agent of formula (I) is present in a concentration of about 0.5 to about 2.0% (w/v).

34. The method of claim 1, wherein the volume of the composition is between about 0.1 to about 1 ml.

35. The method of claim 1 or 29, wherein the animal is a cat.

36. The method of claim 1 or 30, wherein the animal is a dog.

* * * * *